(12) United States Patent
Miyauchi et al.

(10) Patent No.: US 8,768,644 B2
(45) Date of Patent: Jul. 1, 2014

(54) PARTICLE DISTRIBUTION ANALYSIS METHOD FOR COMPUTER READABLE STORAGE MEDIUM FOR STORING PROGRAM FOR EXECUTING THE METHOD

(75) Inventors: Kunio Miyauchi, Nirasaki (JP); Hiroyuki Nakayama, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 380 days.

(21) Appl. No.: 13/175,219

(22) Filed: Jul. 1, 2011

(65) Prior Publication Data

US 2012/0029863 A1 Feb. 2, 2012

Related U.S. Application Data

(60) Provisional application No. 61/365,583, filed on Jul. 19, 2010.

(30) Foreign Application Priority Data

Jul. 2, 2010 (JP) .................................. 2010-152463

(51) Int. Cl.
*G01N 31/00* (2006.01)

(52) U.S. Cl.
USPC ......................................................... 702/128

(58) Field of Classification Search
USPC ......................................................... 702/128
See application file for complete search history.

(56) References Cited

U.S. PATENT DOCUMENTS

| | | | | |
|---|---|---|---|---|
| 5,943,130 A * | 8/1999 | Bonin et al. | ................. | 356/336 |
| 6,118,525 A * | 9/2000 | Fossey et al. | ............. | 356/237.2 |
| 6,528,334 B1 * | 3/2003 | Mizuo et al. | ..................... | 438/16 |
| 6,566,169 B1 * | 5/2003 | Uziel et al. | ..................... | 438/115 |
| 6,738,954 B1 * | 5/2004 | Allen et al. | ....................... | 716/56 |
| 6,936,835 B2 * | 8/2005 | Nishiyama et al. | ...... | 250/559.41 |
| 7,204,912 B2 * | 4/2007 | Saigusa et al. | ........... | 156/345.51 |
| 7,299,104 B2 * | 11/2007 | Tezuka et al. | ................. | 700/112 |
| 7,756,599 B2 * | 7/2010 | Kudo et al. | .................... | 700/121 |
| 7,983,859 B2 * | 7/2011 | Sato | ................................. | 702/59 |
| 2001/0038708 A1 * | 11/2001 | Ishikawa et al. | ............... | 382/141 |
| 2002/0034326 A1 * | 3/2002 | Ishikawa et al. | ............... | 382/149 |
| 2002/0170022 A1 * | 11/2002 | Shirai et al. | ........................ | 716/4 |
| 2003/0202178 A1 * | 10/2003 | Tsuji et al. | .................. | 356/237.2 |
| 2005/0043834 A1 * | 2/2005 | Rotariu et al. | ................... | 700/95 |
| 2005/0062960 A1 * | 3/2005 | Tsuji et al. | .................. | 356/237.2 |

(Continued)

FOREIGN PATENT DOCUMENTS

| JP | 10-326812 A | 12/1998 |
|---|---|---|
| JP | 2008-078392 A | 4/2008 |
| JP | 2009-068946 A | 4/2009 |
| JP | 2009-098123 A | 5/2009 |

*Primary Examiner* — Sujoy Kundu
*Assistant Examiner* — Alvaro Fortich
(74) *Attorney, Agent, or Firm* — Pearne & Gordon LLP

(57) ABSTRACT

There is provided a support method for a particle distribution analysis for a substrate. In the support method, histogram data of inter-particle distances are created for all particles on a target substrate subjected to the particle distribution analysis from particle coordinate data of the target substrate. Further, histogram data of inter-particle distances are created for multiple virtual substrates each having the same number of randomly distributed particles as the particles on the target substrate. Based on a difference between the histogram data of the target substrate and the histogram data of each of the virtual substrates, determination data are created by quantifying a distance between the histogram data of the target substrate and the histogram data of the multiple virtual substrates, and the determination data are displayed on a display unit.

13 Claims, 25 Drawing Sheets

(56) References Cited

U.S. PATENT DOCUMENTS

| | | | |
|---|---|---|---|
| 2005/0206887 A1* | 9/2005 | Morioka et al. | 356/237.5 |
| 2006/0105548 A1* | 5/2006 | Kudo et al. | 438/476 |
| 2008/0013084 A1* | 1/2008 | Matsui et al. | 356/237.5 |
| 2008/0021674 A1* | 1/2008 | Puskas | 702/179 |
| 2008/0228306 A1* | 9/2008 | Yetter et al. | 700/109 |
| 2008/0228418 A1* | 9/2008 | Green | 702/81 |
| 2008/0298670 A1* | 12/2008 | Nakagaki et al. | 382/149 |
| 2009/0050176 A1* | 2/2009 | Pfeuffer | 134/1.3 |
| 2009/0228215 A1* | 9/2009 | Moriya | 702/22 |
| 2009/0299652 A1* | 12/2009 | Nakayama | 702/26 |
| 2010/0188656 A1* | 7/2010 | Matsui et al. | 356/237.3 |
| 2011/0019187 A1* | 1/2011 | Mizukami et al. | 356/335 |
| 2011/0043811 A1* | 2/2011 | Yamane et al. | 356/446 |
| 2011/0172110 A1* | 7/2011 | Merriman | 506/9 |

* cited by examiner

*FIG. 20*

| INTER-PARTICLE DISTANCES OF VIRTUAL SUBSTRATE WV1 ||||||
|---|---|---|---|---|---|
|  | $P_1$ | $\cdots$ | $P_i$ | $\cdots$ | $P_N$ |
| $P_1$ | $d_{11}$ | $\cdots$ | $d_{1i}$ | $\cdots$ | $d_{1N}$ |
| $\vdots$ | $\vdots$ | $\ddots$ | $\vdots$ | $\ddots$ | $\vdots$ |
| $P_i$ | $d_{i1}$ | $\cdots$ | $d_{ii}$ | $\cdots$ | $d_{iN}$ |
| $\vdots$ | $\vdots$ | $\ddots$ | $\vdots$ | $\ddots$ | $\vdots$ |
| $P_N$ | $d_{N1}$ | $\cdots$ | $d_{Ni}$ | $\cdots$ | $d_{NN}$ |

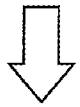

| HISTOGRAM DATA (INTER-PARTICLE DISTANCES) |||||
|---|---|---|---|---|
| CLASS | NUMBER OF PARTICLES ||||
|  | WV1 | $\cdots$ | WVm | $\cdots$ | WVM |
| $d=0$ | $F'_{c1}(0)$ | $\cdots$ | $F'_{cm}(0)$ | $\cdots$ | $F'_{cM}(0)$ |
| $\vdots$ | $\vdots$ |  | $\vdots$ |  | $\vdots$ |
| $d$ | $F'_{c1}(d)$ | $\cdots$ | $F'_{cm}(d)$ | $\cdots$ | $F'_{cM}(d)$ |
| $\vdots$ | $\vdots$ |  | $\vdots$ |  | $\vdots$ |
| $D$ | $F'_{c1}(D)$ | $\cdots$ | $F'_{cm}(D)$ | $\cdots$ | $F'_{cM}(D)$ |

FIG. 21

| STANDARDIZED HISTOGRAM DATA (INTER-PARTICLE DISTANCES) | | | | | |
|---|---|---|---|---|---|
| CLASS | TARGET SUBSTRATE WT | VIRTUAL SUBSTRATES | | | |
| | | WV1 | ... | WVm | ... WVM |
| $d = 0$ | $\overline{F_c}(0)$ | $\overline{F'_{c1}}(0)$ | ... | $\overline{F'_{cm}}(0)$ | ... $\overline{F'_{cM}}(0)$ |
| ⋮ | ⋮ | ⋮ | | ⋮ | ⋮ |
| $d$ | $\overline{F_c}(d)$ | $\overline{F'_{c1}}(d)$ | ... | $\overline{F'_{cm}}(d)$ | ... $\overline{F'_{cM}}(d)$ |
| ⋮ | ⋮ | ⋮ | | ⋮ | ⋮ |
| $D$ | $\overline{F_c}(D)$ | $\overline{F'_{c1}}(D)$ | ... | $\overline{F'_{cm}}(D)$ | ... $\overline{F'_{cM}}(D)$ |

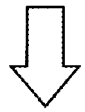

| DIFFERENCE DATA (INTER-PARTICLE DISTANCES) | | | | | |
|---|---|---|---|---|---|
| | TARGET SUBSTRATE WT | VIRTUAL SUBSTRATES | | | |
| | | WV1 | ... | WVm | ... WVM |
| SQUARE ROOT OF SUM OF SQUARE | $[F_c]$ | $[F'_{c1}]$ | ... | $[F'_{cm}]$ | ... $[F'_{cM}]$ |
| NUMBER OF INTERSECTION POINTS | $[|F_c|]$ | $[|F'_{c1}|]$ | ... | $[|F'_{cm}|]$ | ... $[|F'_{cM}|]$ |

FIG. 22A

| STANDARDIZED DIFFERENCE DATA (INTER-PARTICLE DISTANCES) | | | | | |
|---|---|---|---|---|---|
| | TARGET SUBSTRATE | VIRTUAL SUBSTRATES | | | |
| | WT | WV1 | ⋯ | WVm | ⋯ WVM |
| SQUARE ROOT OF SUM OF SQUARE | $\overline{[F_c]}$ | $\overline{[F'_{c1}]}$ | ⋯ | $\overline{[F'_{cm}]}$ | ⋯ $\overline{[F'_{cM}]}$ |
| NUMBER OF INTERSECTION POINTS | $\overline{[\|F_c\|]}$ | $\overline{[\|F'_{c1}\|]}$ | ⋯ | $\overline{[\|F'_{cm}\|]}$ | ⋯ $\overline{[\|F'_{cM}\|]}$ |

FIG. 22B

| STANDARDIZED DIFFERENCE DATA (RADIUSES OF RADIUS VECTORS) | | | | | |
|---|---|---|---|---|---|
| | TARGET SUBSTRATE | VIRTUAL SUBSTRATES | | | |
| | WT | WV1 | ⋯ | WVm | ⋯ WVM |
| SQUARE ROOT OF SUM OF SQUARE | $\overline{[F_R]}$ | $\overline{[F'_{R1}]}$ | ⋯ | $\overline{[F'_{Rm}]}$ | ⋯ $\overline{[F'_{RM}]}$ |
| NUMBER OF INTERSECTION POINTS | $\overline{[\|F_R\|]}$ | $\overline{[\|F'_{R1}\|]}$ | ⋯ | $\overline{[\|F'_{Rm}\|]}$ | ⋯ $\overline{[\|F'_{RM}\|]}$ |

FIG. 22C

| STANDARDIZED DIFFERENCE DATA (POLAR ANGLES OF RADIUS VECTORS) | | | | | |
|---|---|---|---|---|---|
| | TARGET SUBSTRATE | VIRTUAL SUBSTRATES | | | |
| | WT | WV1 | ⋯ | WVm | ⋯ WVM |
| SQUARE ROOT OF SUM OF SQUARE | $\overline{[F_a]}$ | $\overline{[F'_{a1}]}$ | ⋯ | $\overline{[F'_{am}]}$ | ⋯ $\overline{[F'_{aM}]}$ |
| NUMBER OF INTERSECTION POINTS | $\overline{[\|F_a\|]}$ | $\overline{[\|F'_{a1}\|]}$ | ⋯ | $\overline{[\|F'_{am}\|]}$ | ⋯ $\overline{[\|F'_{aM}\|]}$ |

PARTICLE DISTRIBUTION ANALYSIS METHOD FOR COMPUTER READABLE STORAGE MEDIUM FOR STORING PROGRAM FOR EXECUTING THE METHOD

CROSS-REFERENCE TO RELATED APPLICATION

This application claims the benefit of Japanese Patent Application No. 2010-152463 filed on Jul. 2, 2010 and U.S. Provisional Application Ser. No. 61/365,583 filed on Jul. 19, 2010, the entire disclosures of which are incorporated herein by reference in their entirety.

FIELD OF THE INVENTION

The present disclosure relates to a support method for particle distribution analysis for a substrate performed by a substrate processing apparatus, and relates to a computer readable storage medium for storing a program for executing the method.

BACKGROUND OF THE INVENTION

In a substrate processing apparatus for performing a process on a substrate such as a semiconductor wafer, a liquid crystal substrate or a solar cell substrate, particles (foreign substances) on a substrate on which a transfer process or a certain process has been performed are measured. Based on a measurement result, performance of the apparatus is evaluated.

The particle measurement result includes the number or the size (diameter) of the particles, or a particle distribution on the substrate. These measurement results are analyzed together with information (a shape of the apparatus, a gas to be used, a transfer path, a transfer method or the like) of the apparatus, and the analyzed measurement results are used to check the kind or a cause of an abnormality of the apparatus or the process.

Among the particle measurement results, the particle distribution is random in a normal state. If there is an abnormality in the apparatus or the process, the particle distribution on the substrate may have non-uniformity. Accordingly, by determining the abnormality of the particle distribution, it is possible to detect the abnormality of the apparatus or the process.

Japanese Patent Laid-open Publication No. 2009-098123
Japanese Patent Laid-open Publication No. H10-326812
Japanese Patent Laid-open Publication No. 2009-068946
Japanese Patent Laid-open Publication No. 2008-78392

However, the particle distribution is not easy to analyze in comparison with the other measurement results (size, number, etc.). Further, it is very difficult to analyze particle distribution characteristics. Thus, it has been difficult to determine the abnormality of the particle distribution. Accordingly, in order to analyze the particle distribution or detect the abnormality thereof, it is required for an analyzer to have high level of knowledge and experience on the apparatus or the process. Further, there is a difference in determination results depending on analyzers.

Thus, conventionally, the analysis has been focused only on the number, size or composition of the particles (for example, see Patent Documents 1 and 2) among the particle measurement results. Further, until now, an analysis method for detecting the abnormality of the particle distribution has not been established.

Further, there have been conventionally developed analysis methods for a defect distribution, not a particle distribution, on a substrate (for example, see Patent Documents 3 and 4). However, besides the target substrate to be analyzed, these conventional analysis methods also require particle measurement results of other substrates (e.g., normal substrate, etc) for comparison or classification. For example, the abnormality of the particle distribution on the substrate cannot be determined by using a measurement result for only one target substrate.

BRIEF SUMMARY OF THE INVENTION

In view of the above, the present disclosure provides a support method for particle distribution analysis capable of easily determining an abnormality of particle distribution by using a measurement result of only one target substrate.

In accordance with one aspect of the present disclosure, there is provided a support method for particle distribution analysis for a substrate. The support method includes creating target substrate data by calculating inter-particle distances for all particles on a target substrate subjected to the particle distribution analysis from particle coordinate data of the target substrate, classifying the inter-particle distances into multiple classes, calculating the number of particles in each of the multiple classes, generating histogram data indicating the number of particles in each of the multiple classes, and storing the histogram data in a storage unit; creating each virtual substrate data for multiple virtual substrates each having the same number of randomly distributed particles as the particles on the target substrate by calculating inter-particle distances for all particles on each virtual substrate from particle coordinate data, classifying the inter-particle distances on each virtual substrate into multiple classes, calculating the number of particles in each of the multiple classes for each virtual substrate, generating histogram data indicating the number of particles in each of the multiple classes for each virtual substrate, and storing the histogram data in storage unit; creating difference data by calculating an average for the histogram data of the multiple virtual substrates and calculating difference data indicating a difference between the histogram data of the target substrate and the average, and each difference between the histogram data of each virtual substrate and the average, and storing the difference data in the storage unit; creating determination data by calculating determination data quantifying a distance between the histogram data of the target substrate and the histogram data of the multiple virtual substrates based on the difference data, and storing the determination data in the storage unit; and displaying the determination data on a display unit.

In accordance with another aspect of the present disclosure, there is provided a computer readable storage medium storing therein a computer program for executing a support method of a particle distribution analysis for a substrate. The support method includes creating target substrate data by calculating inter-particle distances for all particles on a target substrate subjected to the particle distribution analysis from particle coordinate data of the target substrate, classifying the inter-particle distances into multiple classes, calculating the number of particles in each of the multiple classes, generating histogram data indicating the number of particles in each of the multiple classes, and storing the histogram data in a storage unit; creating each virtual substrate data for multiple virtual substrates each having the same number of randomly distributed particles as the particles on the target substrate by calculating inter-particle distances for all particles on each virtual substrate from particle coordinate data, classifying the inter-particle distances on each virtual substrate into multiple classes, calculating the number of particles in each of the multiple classes for each virtual substrate, generating histogram data indicating the number of particles in each of the multiple classes for each virtual substrate, and storing the histogram data in storage unit; creating difference data by calculating an average for the histogram data of the multiple virtual substrates and calculating difference data indicating a difference between the histogram data of the target substrate and the average, and each difference between the histogram data of each virtual substrate and the average, and storing the difference data in the storage unit; creating determination data by calculating determination data quantifying a distance between the histogram data of the target substrate and the histogram data of the multiple virtual substrates based on the difference data, and storing the determination data in the storage unit; and displaying the determination data on a display unit.

In accordance with the present disclosure, by quantifying a statistical distance between the particle distribution of the target substrate and the random particle distribution of the virtual substrates, it may be possible to determine whether or not the abnormality of the particle distribution of the target substrate is generated. Further, it may be possible to enhance work efficiency for detecting a cause of abnormality. Therefore, it may be possible to determine the abnormality by an analyzer not having high level of knowledge and experience on the apparatus or the process. Further, it may be possible to suppress a difference in determination results. In addition, since the particle distribution characteristics are easily checked by the histogram data of the inter-particle distances, by quantifying the particle distribution by the histogram data of the inter-particle distances, it may be possible to effectively enhance determination accuracy.

Further, by obtaining the particle measurement result of the target substrate, the histogram of the inter-particle distances of the target substrate may be generated from the particle coordinate data, and the histogram of the inter-particle distances of the multiple virtual substrates each having the same number of randomly distributed particles as the particles on the target substrate may be generated. Accordingly, the difference data or the determination data may be created by using the histogram of the inter-particle distances of the target substrate and the histogram of the inter-particle distances of the multiple virtual substrates. As described above, in accordance with the present disclosure, by using the particle measurement result of only one target substrate, it may possible to create the determination data used for determining the abnormality of the particle distribution.

The creating difference data may include calculating an average and a standard deviation for the number of particles in each of the multiple classes of the histogram data of the virtual substrates; standardizing the number of particles in each of the multiple classes of the histogram data of the target substrate and the virtual substrates by using the average and the standard deviation for the number of particles in each of the multiple classes of the histogram data of the virtual substrates, and generating standardized histogram data of the target substrate and the virtual substrates, and storing the standardized histogram data of the target substrate and the virtual substrates in the storage unit; calculating the number of intersection points of the particle number and a square root of sum of square of the particle number from the standardized histogram data of the target substrate and the virtual substrates; calculating an average and a standard deviation of the number of intersection points of the particle number and the square root of sum of square in the standardized histogram data of the virtual substrates; and standardizing the number of intersection points of the particle number and the square root of sum of square of the particle number of the standardized histogram data of the target substrate and the virtual substrates by using the average and the standard deviation of the standardized histogram data of the virtual substrates, and storing the standardized number of intersection points of the particle number and the standardized square root of sum of square of the particle number, as the difference data, in the storage unit. Therefore, by using the average and the standard deviation of the histogram data of the virtual substrates for standardizing, it may be possible to create the histogram data or the difference data which are not dependent on the number of particles or the size of the substrate.

The creating determination data may include calculating a Mahalanobis distance from the difference data and storing the Mahalanobis distance as the determination data in the storage unit. Therefore, it may be possible to display the determination data as a value capable of easily determining the determination data. Here, the displaying the determination data may include displaying the determination data on the display unit, and abnormality of the determination data when the determination data is greater than or equal to a certain threshold value. Therefore, it may be possible to determine at a glance whether or not the abnormality of the particle distribution is generated.

In the displaying the determination data on a display unit, difference data of the number of intersection points between the target substrate and all the virtual substrates, and difference data of the square root of sum of square between the target substrate and all the virtual substrates may be respectively plotted on a vertical axis and a horizontal axis, or vice versa. Further, in the displaying the determination data on a display unit, difference data of the square root of sum of square calculated from the radiuses between the target substrate and all the virtual substrates, and difference data of the square root of sum of square calculated from the polar angles between the target substrate and all the virtual substrates may be respectively plotted on a vertical axis and a horizontal axis, or vice versa. Therefore, it may be possible to determine at a glance whether or not the abnormality of the particle distribution is generated. Further, it may be possible to check at a glance a separated distance between the difference data of the target substrate and the difference data of the virtual substrates.

In the displaying the determination data on a display unit, each histogram may be generated by calculating the inter-particles distances, and the histogram of the target substrate and average histogram of the virtual substrates generated by averaging the numbers of each class in the histogram data of the virtual substrates may be displayed on the display unit. Further, in the displaying the determination data on a display unit, each histogram may be generated by calculating the radiuses of the radius vectors, and the histogram of the target substrate and average histogram of the virtual substrates generated by averaging the numbers of each class in the histogram data of the virtual substrates may be displayed on the display unit. Furthermore, in the displaying the determination data on a display unit, each histogram may be generated by calculating the polar angles of the radius vectors, and the histogram of the target substrate and average histogram of the virtual substrates generated by averaging the numbers of each class in the histogram data of the virtual substrates may be displayed on the display unit.

In the displaying the determination data on a display unit, each histogram may be generated by calculating the radiuses of the radius vectors, and the radiuses of one or more classes, having a large number difference between the histogram data of the target substrate and average for the histogram data of the virtual substrates in descending order, in each class of the histogram data of the target substrate may be displayed on a map of the particle coordinate data. Further, in the displaying the determination data on a display. unit, each histogram may be generated by calculating the polar angles of the radius vectors, and the polar angles of one or more classes, having a large number difference between the histogram data of the target substrate and average for the histogram data of the virtual substrates in descending order, in each class of the histogram data of the target substrate may be displayed on a map of the particle coordinate data. Therefore, it may be possible to check at a glance the difference between the average histogram of the virtual substrates and the histogram of the target substrate.

In accordance with the present disclosure, by using the particle measurement result of only one target substrate, it may be possible to quantifying the particle distribution analysis result. Thus, without special expert knowledge or experience, it can be possible to very easily determine whether or not an abnormality of the particle distribution is generated.

BRIEF DESCRIPTION OF THE DRAWINGS

FIG. 20 is a diagram showing examples of inter-particle distances and histogram data of virtual substrates.

FIG. 21 is a diagram showing examples of standardized histogram data and difference data of an inter-particle distance.

FIG. 22A is diagram showing an example of standardized difference data of inter-particle distances.

FIG. 22B is diagram showing an example of standardized difference data of radiuses of radius vectors for particle positions.

FIG. 22C is diagram showing an example of standardized difference data of polar angles of radius vectors for particle positions.

DETAILED DESCRIPTION OF THE INVENTION

Figure 1:
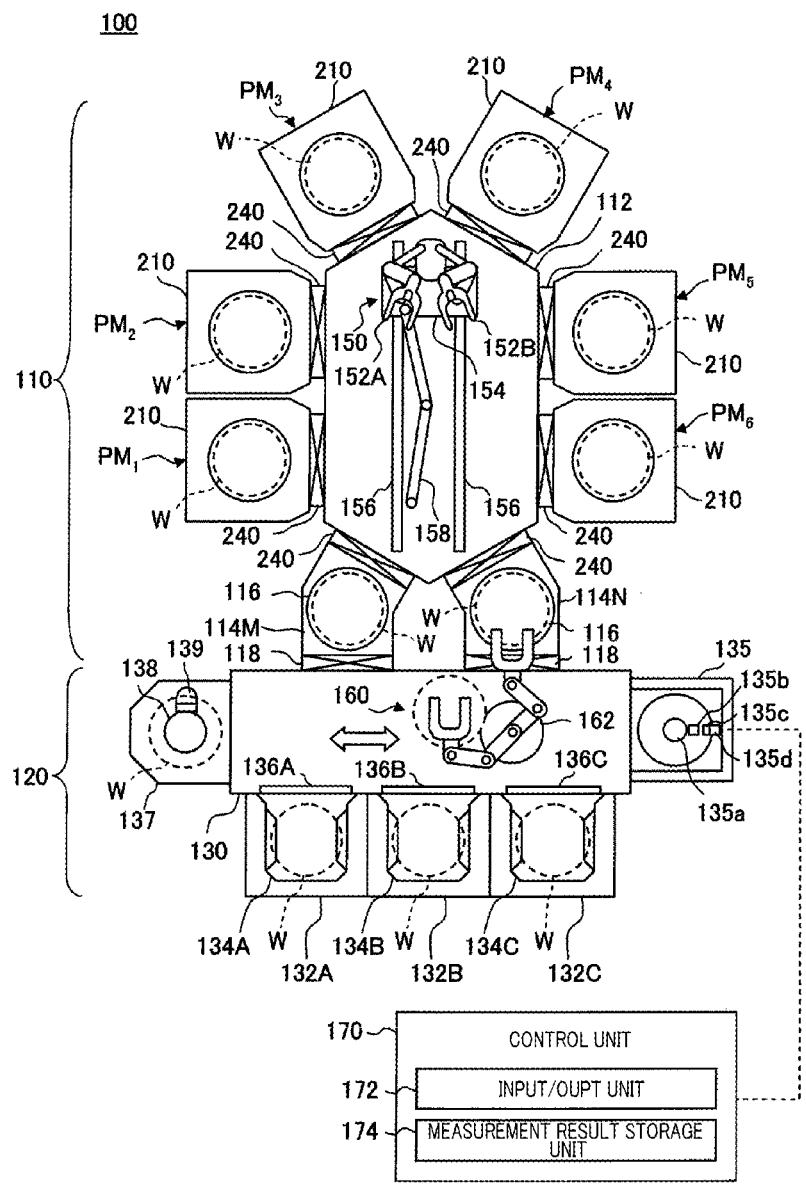
FIG. 1 is a cross sectional view showing a configuration example of a substrate processing apparatus for performing a process on a substrate and particle distribution analysis in accordance with an embodiment of the present disclosure.

Hereinafter, the embodiments of the present disclosure will be described in detail with reference to the accompanying drawings. Through the present specification and drawings, parts having substantially same function and configuration will be assigned same reference numerals, and redundant description thereof will be omitted.

(Configuration Example of Substrate Processing Apparatus)

First, a substrate processing apparatus for performing a process on a substrate subjected to a particle distribution analysis supporting method in accordance with the present disclosure will be described. FIG. 1 is a cross sectional view showing a schematic configuration of a substrate processing apparatus. The substrate processing apparatus 100 may include a processing unit 110 having a multiple number of (here, six) plasma processing apparatuses $PM_1$ to $PM_6$ for performing a process on a substrate W serving as a semiconductor wafer; a transfer unit 120 for loading and unloading the substrate W into and from the processing unit 110 under an atmospheric atmosphere; and a control unit 170 for controlling an entire operation of the substrate processing apparatus 100.

Here, there will be explained each of the plasma processing apparatuses PM$_1$ to PM$_6$ as a plasma etching apparatus. The plasma processing apparatuses PM$_1$ to PM$_6$ may have the same configuration. That is, each of the plasma processing apparatuses PM$_1$ to PM$_6$ may include a processing chamber 210, and plasma of a processing gas is generated on the substrate W placed within the processing chamber 210. Accordingly, a plasma etching process may be performed on a surface of the substrate W.

Further, in the substrate processing apparatus 100 shown in FIG. 1, it is described that the six plasma processing apparatuses are provided. However, the present disclosure is not limited thereto, and five or less plasma processing apparatuses may be provided. Moreover, in the substrate processing apparatus 100 shown in FIG. 1, the plasma processing apparatuses may not be same, and processing apparatuses (e.g., heat treating apparatus, film forming apparatus or the like) for performing other processes than the etching process may be provided.

A transfer chamber 130 of the transfer unit 120 may be formed in a box body having a substantially rectangular cross sectional shape, and an inert gas such as a N$_2$ gas or a clean air may be circulated in the transfer chamber 130. Provided at one side of the transfer chamber 130 may be a multiple number of cassette tables 132A to 132C. Cassette containers 134A to 134C may be mounted on the cassette tables 132A to 132C, respectively. Further, in the transfer chamber 130, three loading ports 136A to 136C as inlet ports for the substrate W may be provided so as to correspond to the cassette tables 132A to 132C, respectively.

In FIG. 1, although it is shown, by way of example, that each of three cassette containers 134A to 134C is mounted on each of the cassette tables 132A to 132C, respectively, the numbers of the cassette tables and the cassette containers are not limited thereto. By way of example, they may be one or two, or four or more.

Each of the cassette containers 134A to 134C may accommodate at least one lot (e.g., 25 sheets) of substrates W in multi-layers at a same pitch. The inside of each cassette container 134A to 134C may be airtightly sealed under, e.g., a N$_2$ gas atmosphere. Further, the substrates W may be loaded into and unloaded from the inside of the transfer chamber 130 through the loading ports 136A to 136C.

In the transfer chamber 130, there may be provided a transfer unit side transfer device 160 including, e.g., a contractible-extendible/elevatable/rotatable multi-joint arm. The transfer unit side transfer device 160 may transfer the substrate W by sliding along a lengthwise direction (marked by an arrow in FIG. 1) thereof. Specifically, the transfer unit side transfer device 160 may be fixed on a base 162, and the base 162 may be slidably movable by, e.g., a linear motor driving device on a non-illustrate guide rail provided at a center of the transfer chamber 130 along the lengthwise direction thereof. The transfer unit side transfer device 160 may be, e.g., a double-arm device having two picks as shown in FIG. 1 or may be a single-arm device having one pick.

A particle measurement room (particle monitor) 135 may be provided at one end of the transfer chamber 130. In the particle measurement room 135, it may be possible to measure distribution, number and size of particles on the substrate W. In the present disclosure, the particle distribution may be analyzed.

The particle measurement room 135 may include a rotatable mounting table 135a for mounting the substrate W thereon; a light source 135b for irradiating a laser beam toward the substrate W; a light receiving unit 135c for receiving scattered light on the substrate W after being irradiated from the light source 135b; and a signal processing unit 135d for processing a light receiving signal received by the light receiving unit 135c.

The light source 135b, the light receiving unit 135c and the signal processing unit 135d may serve as optical units. Every optical unit can be moved along radiuses of radius vectors of the substrate W. Accordingly, by moving the optical units between on a center of the substrate W and on an edge thereof while rotating the substrate W held on the mounting table 135a, particles on the entire surface of the substrate W can be measured.

The signal processing unit 135d may be connected to the control unit 170. Accordingly, the control unit 170 may receive particle data (e.g., pixel data) on the substrate W through the signal processing unit 135d. The control unit 170 may create particle coordinate data (particle map) on a substrate surface based on the received data, and may store the particle map in a measurement result storage unit 174. Here, the particle map may be created by mapping the particle coordinate data. Further, the configuration of the particle measurement room 135 is not limited to the above-described example.

An orienter (pre-alignment stage) 137 as a positioning device may be provided at the other end of the transfer chamber 130. The orienter 137 may include, by way of example, a rotary mounting table 138 and an optical sensor 139 for optically detecting a periphery of the substrate W. The orienter 137 may detect an orientation flat or a notch of the substrate W, and align a position of the substrate W.

Hereinafter, a configuration example of the processing unit 110 will be described. Since the substrate processing apparatus 100 in accordance with the present embodiment serves as a clustered substrate processing apparatus, the processing unit 110 may include a common transfer chamber 112 having a polygonal (e.g., hexagonal) cross sectional shape, as shown in FIG. 1. The plasma processing apparatuses PM$_1$ to PM$_6$ may be arranged around the common transfer chamber 112 and connected to the common transfer chamber 112 via gate valves 240, respectively.

Further, front ends of a first load lock chamber 114M and a second load lock chamber 114N may be also connected to the common transfer chamber 112 via gate valves (vacuum side gate valves) 240, respectively. Meanwhile, base ends of the first and the second load lock chamber 114M and 114N may be connected to the other side of the transfer chamber 130 via gate valves (atmosphere side gate valves) 118. Here, the other side of the transfer chamber 130 may be a long side of the transfer chamber 130 having a substantially polygonal cross sectional shape.

The inside of the common transfer chamber 112 may be adjusted to a certain vacuum pressure. The common transfer chamber 112 may load and unload the substrate W between the processing chambers 210, or between the respective processing chambers 210 and the first load lock chamber 114M (the second load lock chamber 114N) within the plasma processing apparatuses PM$_1$ and PM$_6$.

The first and the second load lock chamber 114M and 114N may adjust an internal pressure thereof while holding the substrate W temporarily therein, and then, transfer the substrate W to the next chamber. A transit table 116 for mounting thereon the substrate W may be provided in each of the first and the second load lock chamber 114M and 114N.

In the common transfer chamber 112, there may be a processing unit side transfer device 150 including, e.g., a contractible-extendible/elevatable/rotatable multi-joint arm. The processing unit side transfer device 150 may have two picks 152A and 152B, and, thus, two sheets of substrates can be simultaneously handled by the processing unit side transfer device 150.

The processing unit side transfer device 150 may be rotatably supported at a base 154. The base 154 may be slidably movable on a guide rail 156 extended from a base end to a front end of the inside within the common transfer chamber 112 by, e.g., a non-illustrate slide driving motor. Further, a flexible arm 158 for wiring of, e.g., an arm rotating motor may be connected to the base 154.

In accordance with the processing unit side transfer device 150 configured as described above, by slidably moving the processing unit side transfer device 150 along the guide rail 156, the processing unit side transfer device 150 can be accessed to the first and the second load lock chamber 114M and 114N, and the respective processing chambers 210 of the plasma processing apparatuses $PM_1$ to $PM_6$. By way of example, when the processing unit side transfer device 150 is accessed to the first and the second load lock chamber 114M and 114N and the respective processing chambers 210 of the plasma processing apparatuses $PM_1$ and $PM_6$ arranged to face each other, the processing unit side transfer device 150 may be located near the base end of the common transfer chamber 112 on the guide rail 156.

Meanwhile, when the processing unit side transfer device 150. is accessed to the respective processing chambers 210 of the other four plasma processing apparatuses $PM_2$, $PM_3$ $PM_4$ and $PM_5$, the processing unit side transfer device 150 may be located near the front end of the common transfer chamber 112 on the guide rail 156. Accordingly, the single processing unit side transfer device 150 can be accessed to all of the processing chambers 210 and the first and second load lock chamber 114M and 114N connected to the common transfer chamber 112.

Further, the configuration of the processing unit side transfer device 150 is not limited to the above-described configuration, and, by way of example, two transfer devices may be used as the processing unit side transfer device 150. That, is, a first transfer device including a contractible-extendible/elevatable/rotatable multi-joint arm may be provided near the base end of the common transfer chamber 112, and a second transfer device including a contractible-extendible/elevatable/rotatable multi-joint arm may be provided near the front end of the common transfer chamber 112. Moreover, the number of the picks of the processing unit side transfer device 150 is not limited to two. By way of example, only one pick may be provided.

The components such as the respective plasma processing apparatuses $PM_1$ to $PM_6$, the orienter 137, the particle measurement room 135 or the transfer devices 150 and 160 may be controlled in response to a control signal from the control unit 170. The control unit 170 may control each component based on a certain program and perform the process on the substrate.

The control unit 170 may include an input/output unit 172 for inputting and outputting various data by an operator; and the measurement result storage unit 174 for storing therein processing conditions (processing recipes) for processing the substrate or data such as particle coordinate data (particle map) measured, in the particle measurement room 135. Besides, although not shown, the control unit 170 may include a controller for controlling each component of the substrate processing apparatus 100.

Specifically, the controllers may include a controller for controlling each component besides controllers for the transfer devices 150 and 160 and a controller for the orienter 137. Further, it may be possible to provide each controller for each plasma processing apparatus $PM_1$ to $PM_6$, and each component of the plasma processing apparatuses $PM_1$ to $PM_6$ may be controlled by the respective controllers. In this case, the control unit 170 may be connected with the respective controllers of the plasma processing apparatuses $PM_1$ to $PM_6$ and control the substrate processing apparatus 100 while exchanging data or signals therebetween.

The input/output unit 172 may include an input unit such as a keyboard, a mouse or a touch panel; a display unit such as a display for displaying and outputting various information; and a drive device for reading and writing a storage medium such as a Floppy Disk (Registered Trademark), a CD-ROM or the like.

When the particles on the substrate are measured by the substrate processing apparatus 100 having the above-described configuration, the target substrate may be transferred into the particle measurement room 135 and mounted on the mounting table 135a. Then, while rotating the substrate W held on the mounting table 135a in the particle measurement room 135, by moving the optical units between from the center of the substrate W and to the edge thereof, the particles on the entire surface of the substrate W can be measured. Here, data on the particles (e.g., pixel data) may be transmitted to the control unit 170. Then, particle coordinate data (particle map) may be created by the control unit 170 and stored in the measurement result storage unit 174.

The measurement result storage unit 174 may not be provided in the control unit 170 and may be provided in, by way of example, a data processing apparatus (e.g., an AGC (Advanced Group Controller)) as a data processing computer connected to the control unit 170 through a network. In such a case, the control unit 170 may transmit data on the particles (particle coordinate data, etc.) measured by the substrate processing apparatus 100 to the data processing apparatus through the network, and the data processing apparatus may store the transmitted data in the measurement result storage unit 174 of a storage unit such as a hard disk.

The data processing apparatus may include a drive device for reading and writing a storage medium such as a Floppy Disk (Registered Trademark) or a CD-ROM. The particle coordinate data (particle map) stored in the measurement storage unit 174 may be stored in the storage medium.

Such data processing apparatus may serve as a particle distribution analysis supporting apparatus. Further, the data processing apparatus may perform, in addition to the above processes, an analysis process or a statistical process of process data, or a monitoring process for the process data, an analysis result or a statistical result thereof. Furthermore, the data processing apparatus may perform a process for applying the analysis result or the statistical result thereof to recipes. The data processing apparatus may include a single computer, or may include a multiple number of computers. Moreover, the data processing apparatus may be configured as a client-server system so as to distribute the above-mentioned functions to a server and clients.

(Configuration Example of Particle Distribution Analysis Supporting Apparatus)

Figure 2:
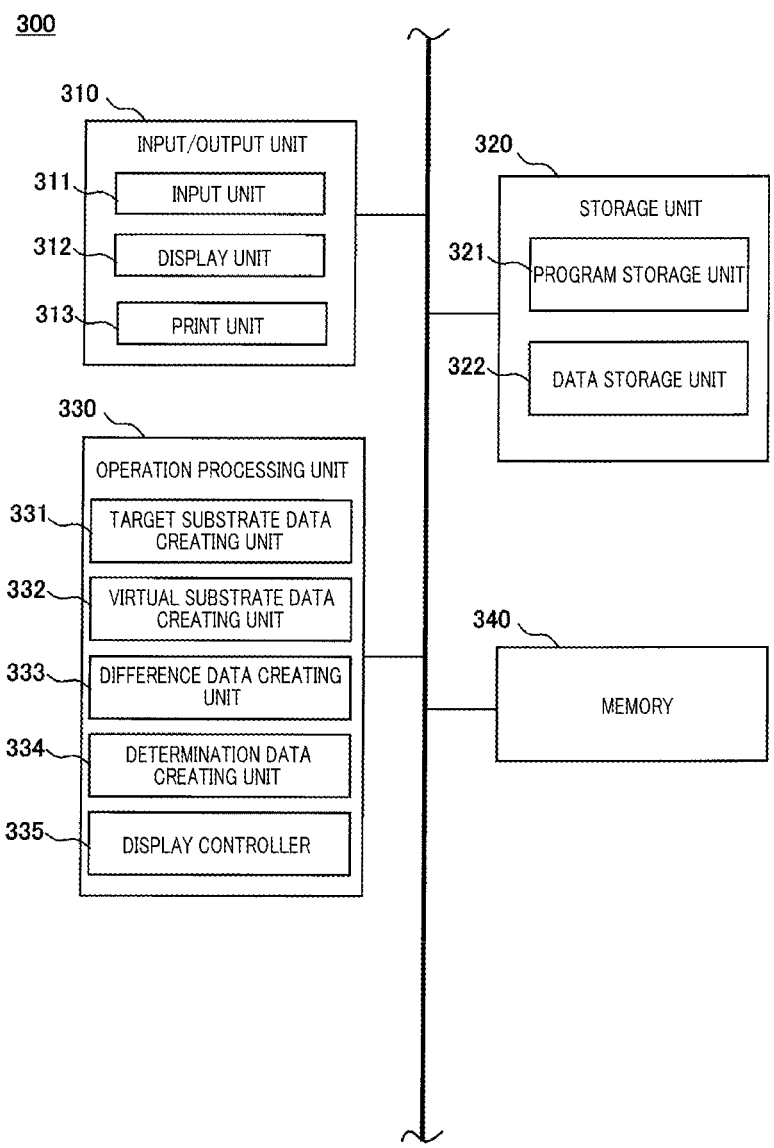
FIG. 2 is a block diagram showing a configuration of a particle distribution analysis supporting apparatus in accordance with the present embodiment.

Hereinafter, a configuration example of the particle distribution analysis supporting apparatus of the present disclosure will be described with reference to the drawing. FIG. 2 is a block diagram showing a configuration of a particle distribution analysis supporting apparatus in accordance with the present embodiment.

As illustrated in FIG. 2, the particle distribution analysis supporting apparatus 300 may include an input/output unit 310 for performing an input operation and an output (display) operation by an operator; an operation processing unit 330 for performing various operation processes; a storage unit 320 for storing therein data required for the operation processes of the operation processing unit 330; and a memory 340 for temporarily storing an operation results by the operation processing unit 330.

The input/output unit 310 may include an input unit 311 such as a keyboard, a mouse or a touch panel; a display unit 312 such as a display for displaying various information; and a print unit 313 for printing display results. Although it is not illustrated, the input/output unit 310 may have, in addition to the above components, a drive device for reading and writing a storage medium such as a Floppy (registered trademark) disc or a CD-ROM.

The storage unit 320 may include a program storage unit 321 such as a hard disk for storing a required program for performing a particle distribution analysis process; and a data storage unit 322 for storing files or data used for performing the particle distribution analysis supporting process.

The data storage unit 322 may store data such as measurement results in the particle measurement room 135. Specifically, by way of example, the data storage unit 322 may store the measurement results inputted from a storage medium such as a Floppy (registered trademark) disc or a CD-ROM storing therein the measurement results stored in the measurement result storage unit 174 of the control unit 170 of the substrate processing apparatus 100 (or the storage unit of the data processing apparatus connected to the control unit 170 through the network).

By way of example, when the control unit 170 of the substrate processing apparatus 100 is connected to the particle distribution analysis supporting apparatus 300 via the network, the particle distribution analysis supporting apparatus 300 may store, in the data storage unit 322, the measurement result such as particle coordinate data (particle map) received from the control unit 170 via the network. Further, when the measurement result is stored in the data processing apparatus connected to the network, the particle distribution analysis supporting apparatus 300 may store, in the data storage unit 322, the measurement result received from the data processing apparatus via the network.

The operation processing unit 330 may include, e.g., a CPU (Central Processing Unit), and perform, based on the program, the particle distribution analysis supporting process in accordance with the present embodiment. The operation processing unit 330 may serve as various processing units for performing the particle distribution analysis supporting process by executing a particle distribution analysis supporting program stored in the program storage unit 321. Specifically, the operation processing unit 330 may serve as a target substrate data creating unit 331, a virtual substrate data creating unit 332, a difference data creating unit 333, a determination data creating unit 334 and a display controller 335.

Hereinafter, the above-mentioned processes will be described with reference to a sequence of the particle distribution analysis supporting process. Herein, there will be described a case of using an inter-particle distance as an indicator for particle distribution characteristics in the particle distribution analysis.

First of all, the target substrate data creating unit 331 may create particle coordinate data (particle map) of a target substrate WT to be subjected to the particle distribution analysis from the actual measurement result in the particle measurement room 135. Thereafter, the target substrate data creating unit 331 may create histogram data as an indicator for the particle distribution characteristics (inter-particle distances, radiuses and polar angles of radius vectors for particle positions) on the target substrate WT based on the created particle coordinate data.

Figure 3:
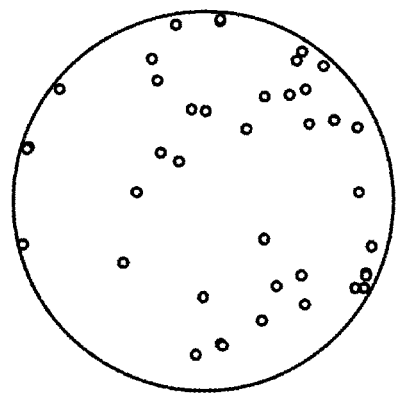
FIG. 3 is a diagram showing a specific example of particle distribution.
Figure 4:
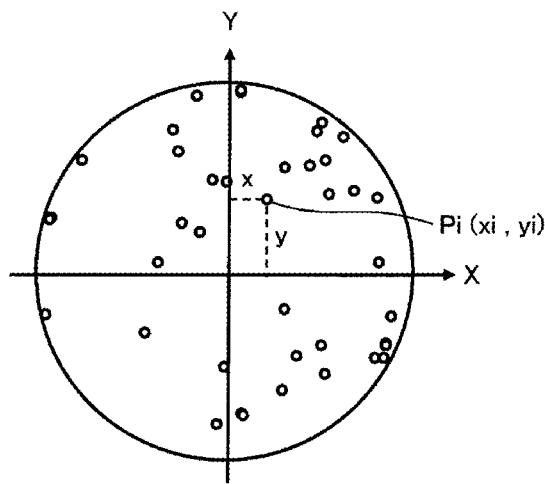
FIG. 4 is a diagram for describing particle coordinate data when particle coordinates are expressed as Cartesian coordinates.
Figure 5:
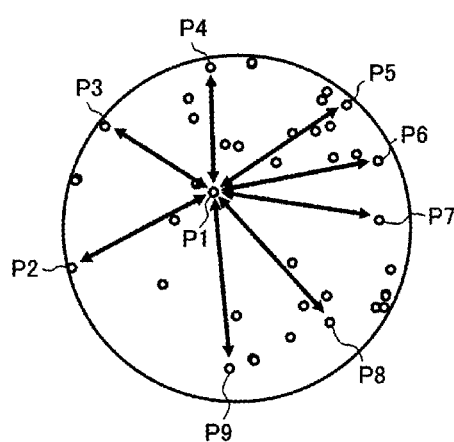
FIG. 5 is a diagram for describing inter-particle distances.

Specifically, as shown in FIG. 5, the inter-particle distances may be calculated from the particle coordinate data. Here, the particle coordinate data may be obtained by expressing the particle distribution on the target substrate WT shown in FIG. 3 as Cartesian coordinates (XY coordinates) shown in FIG. 4. FIG. 5 conceptually shows inter-particle distances between a particle P1 and other particles P2 to P9. In this way, inter-particle distances between each of particles P1 to PN and other particles on a single target substrate may be calculated, as can be seen from FIG. 6. Moreover, single histogram data may be created based on the calculated inter-particle distances, and the histogram data may be stored as target substrate data in the data storage unit 322. Here, the inter-particle distances may be classified into multiple classes, and the number of particles in each of the multiple classes may be calculated. In this way, the histogram data indicating the number of particles in each of the multiple classes may be generated.

Figure 6:
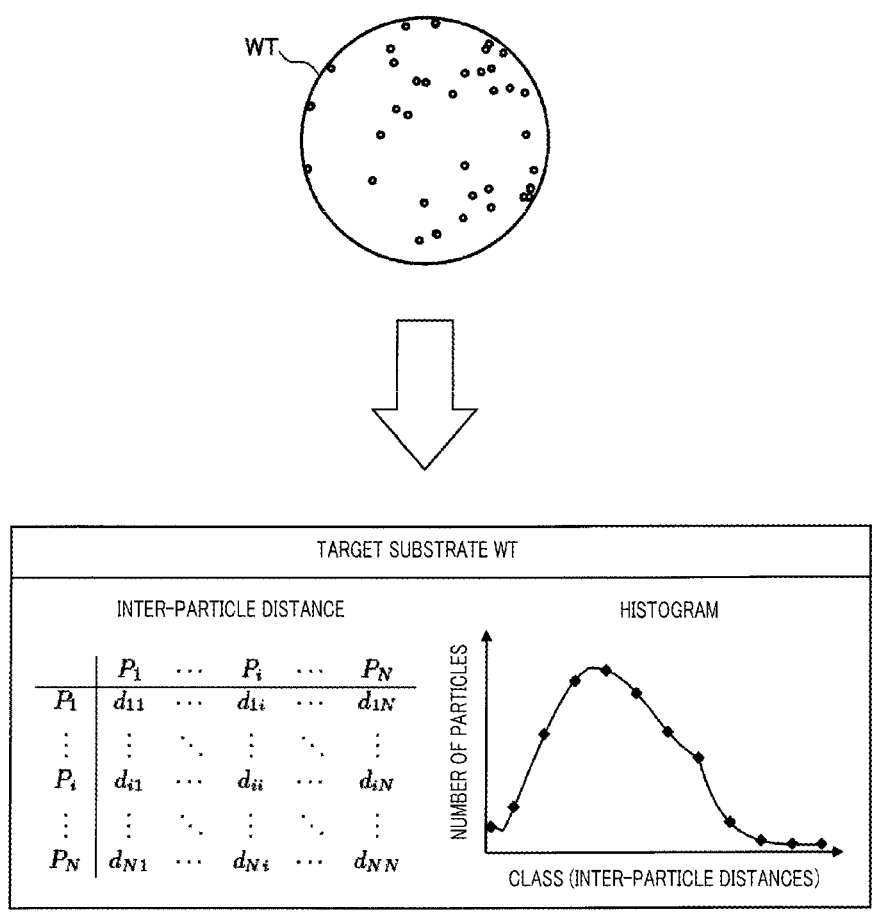
FIG. 6 is a diagram for describing a target substrate data creating process.

As shown in FIG. 6, in the histogram data of the inter-particle distances, the horizontal axis represents the inter-particle distance. That is, as the inter-particle distance is closer to an origin, the number (frequency) of particles having relatively short inter-particle distances may be marked. Meanwhile, as the inter-particle distance is far from the origin, the number (frequency) of particles having relatively long inter-particle distances may be marked. Further, the inter-particle distance is zero (d=0) when the particle itself is marked. Accordingly, if only a single particle exists in the same coordinate, the number of particles marked in origin (i.e., d=0) may be equal to the total number of particles on the substrate.

Next, the virtual substrate data creating unit 332 may create inter-particle distances for all particles on a multiple number of (M-number of) virtual substrates WV each having the same number of randomly distributed particles as the particles on the target substrate WT. Thereafter, the virtual substrate data creating unit 332 may generate histogram data based on the inter-particle distances. Here, the particle distributions on the virtual substrates WV are made by virtual particle distributions on the virtual substrates which does not exist in reality but created by calculation of a computer.

Specifically, as in the case of the target substrate WT, the virtual substrate data creating unit 332 may calculate the inter-particle distances between each of particles P1 to PN and other particles on a single virtual substrate WV having the same number of randomly distributed particles as the particles on the target substrate WT. Thereafter, the virtual substrate data creating unit 332 may generate the single histogram data based on the inter-particle distances. In this way, as shown in FIG. 7, the virtual substrate data creating unit 332 may generate the histogram data for the respective M-number of virtual substrates WV1 to WVM, and then may store the histogram data for the respective M-number of virtual substrates WV1 to WVM as virtual substrate data in the data storage unit 322.

If the histogram data of the virtual substrates WV1 to WVM each having randomly distributed particles are averaged, the average histogram data of the virtual substrates WV1 to WVM may have a specific shape depending on the number of particles. A difference between the specific shape of the average histogram of the virtual substrates WV and a shape of the histogram of the target substrate WT may be quantified. Accordingly, determination data may be calculated to determine an abnormality of the particle distribution.

The difference between the histograms may be quantified by a difference data creating unit 333 and a determination data creating unit 334 which will be described below.

Figure 7:
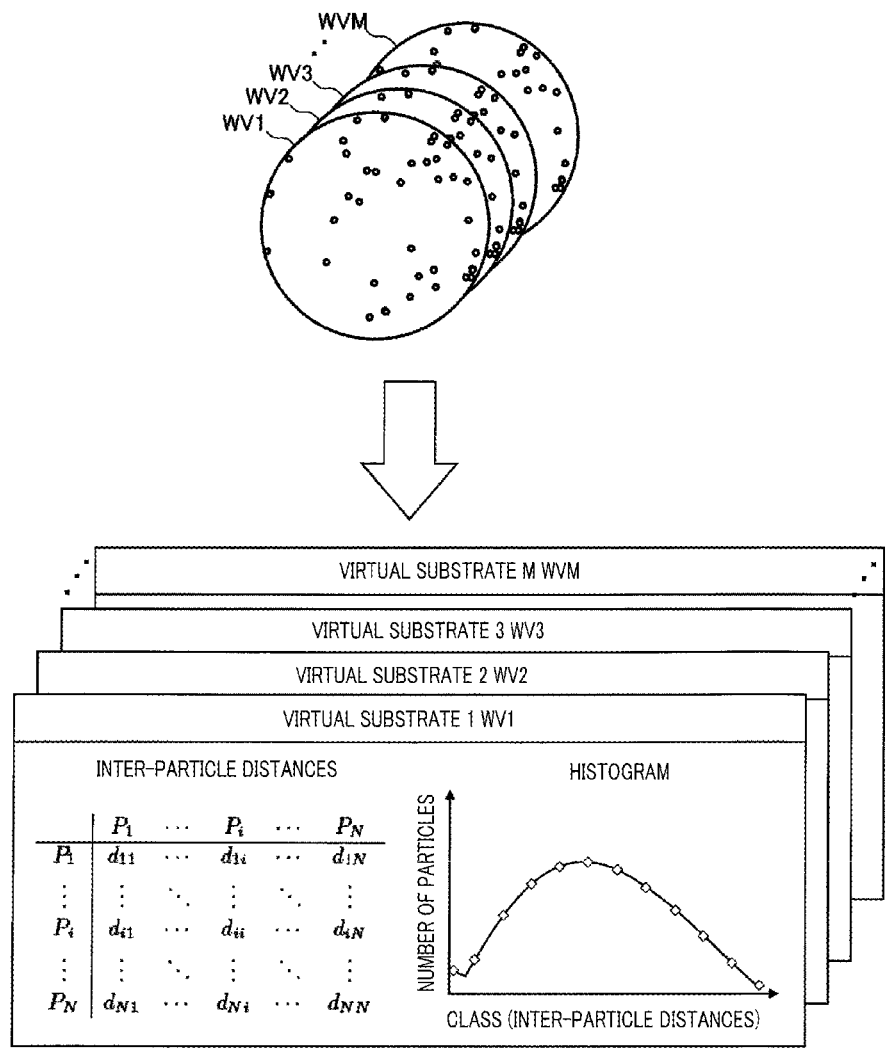
FIG. 7 is a diagram for describing a virtual substrate data creating process.
Figure 8:
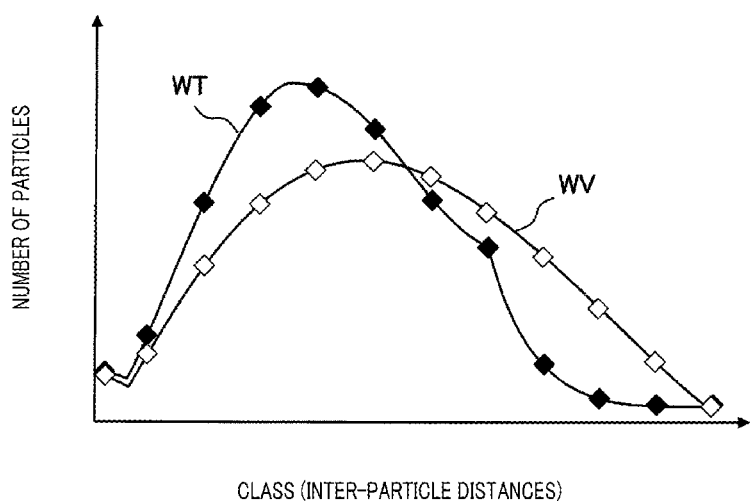
FIG. 8 is a diagram for describing a difference data creating process for creating difference data between histograms of a target substrate and virtual substrates.

The difference data creating unit 333 may calculate the average for the histogram data of the virtual substrates WV1 to WVM shown in FIG. 7, and create difference data indicating the difference between the average histogram of the virtual substrates WV1 to WVM and the histogram of the target substrate WT shown in FIG. 6. Thereafter, the difference data creating unit 333 may store the difference data in the data storage unit 322. As illustrated in FIG. 8, the difference data may be used for quantifying the difference between the histogram data of the target substrate WT and the average histogram data of the virtual substrates WV. The difference data may include, e.g., sum of arithmetic averages of the histograms, sum of absolute averages of the histograms, square root of sum of square of the histograms, the number of intersection points where the histograms intersect with each other, or the like.

In the present embodiment, the square root of sum of square and the number of intersection points are used as the difference data. The square root of sum of square can be effectively used as the difference data, because the square root of sum of square is increased as the difference in the shapes of the two histograms becomes greater. In addition, the number of intersection points can also be effectively used as the difference data, because the number of intersection points is increased as the shapes of the two histograms are similar and the difference of the histograms is remarkable.

Thereafter, the determination data creating unit 334 may create the difference data indicating the difference between the virtual substrates WV1 to WVM and the target substrate WT as a single indicator for easy determination. Here, the indicator may be calculated by quantifying the difference between the virtual substrates WV1 to WVM and the target substrate WT by a statistical method (e.g., Mahalanobis distance). Then, the determination data creating unit 334 may store the indicator as the determination data in the data storage unit 322. By creating the difference data as the indicator for easy determination, it may be possible to easily check a separated distance between the histogram data of the target substrate WT and the histogram data of the virtual substrates WV each having randomly distributed particles. Moreover, since the quantified determination data is compared with a certain threshold value, the abnormality can be easily determined depending on whether or not the quantified determination data exceeds the threshold value.

Especially, in the present embodiment, the determination data may be calculated by, as an indicator, the inter-particle distances indicating the particle distribution characteristics. Therefore, as will be described later, the determination data may have a considerably different value between when the particle distribution is abnormal and when the particle distribution is normal. For this reason, even when it is difficult to determine the abnormality of the particle distribution (particle map) at a glance, the abnormality of the particle distribution (particle map) can be easily determined by the determination data.

Figure 9:
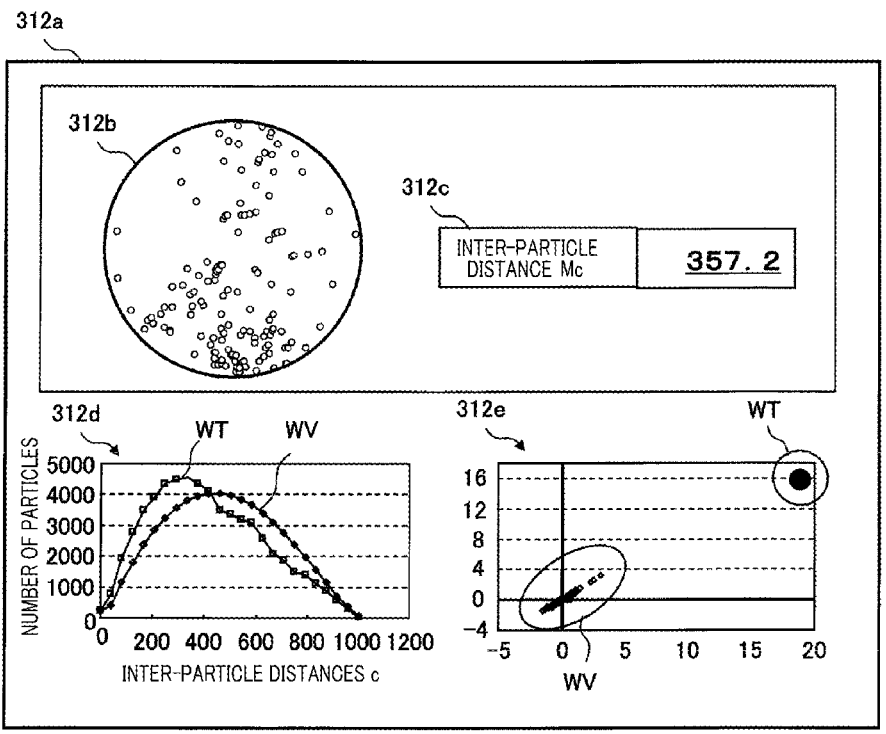
FIG. 9 is a diagram showing an example of displaying an analysis result of inter-particle distances.

Thereafter, the display controller 335 may create display data by mapping the determination data, the histogram data and the difference data, and display the display data on the display unit 312. FIG. 9 shows a specific example of displaying the display data on a screen 312a of the display unit 312. FIG. 9 shows an example of displaying, on the screen 312a, a particle map 312b visualized on the substrate, inter-particle distance determination data 312c calculated by the Mahalanobis distance from the difference data, an inter-particle distance histogram 312d, a difference map 312e visualizing the difference data of the target substrate WT and the difference data of the virtual substrates WV1 to WVM by mapping the difference data. Furthermore, it may be determined whether or not the determination data exceeds the certain threshold value. When it is determined that the determination data exceeds the certain threshold value, the display controller 335 may display the abnormality of the determination data. The abnormality of the determination data can be expressed by highlighting the determination data by, e.g., underline, bold characters, shading, inverse characters, decorative characters or the like. Accordingly, the abnormality can be easily determined.

The square root of sum of square and the number of intersection points may be respectively calculated as the difference data of the histograms. On the difference map 312e, a horizontal axis may represent the difference data of the square root of sum of square and a vertical axis may represent the difference data of the number of intersection points. Here, the difference data may be standardized by using the average and a standard deviation of all the virtual substrates WV1 to WVM. Therefore, an origin of the difference map may be the average, and the standard deviation of the difference map may be about 1. Accordingly, it may be possible to create the data which is not dependent on the number of particles or the size of the substrate. The calculation method for the standardization will be described in detail later.

The display data shown in FIG. 9 may be checked in the following manner. First of all, when the determination data 312c is greater than or equal to the threshold value of, e.g., about 4, it may be determined that the particle distribution is abnormal. On the other hand, when the determination data 312c is smaller than the threshold value of about 4, it may be determined that the particle distribution is normal. In FIG. 9, since the determination data 312c is about 357.2 considerably greater than the threshold value, it may be determined that the particle distribution is abnormal. Furthermore, the threshold value for determining abnormality is not limited to the above.

Besides, from the difference map 312e, it may be possible to visually check a separated distance between the difference data of the target substrate WT and the difference data of the virtual substrates WV each having randomly distributed particles. As the difference data of the target substrate WT becomes farther from the difference data of the virtual substrates WV, it may be determined that the abnormality of the particle distribution is serious. By way of example, as can be seen from the difference map 312e illustrated in FIG. 9, the difference data of the target substrate WT is far from the difference data of the virtual substrates WV. Accordingly, it may be visually determined that the abnormality of the particle distribution is serious.

In addition, as shown in FIG. 9, by standardizing the difference data by the average and the standard deviation of the virtual substrates WV, the origin of the difference map 312e is the average of the virtual substrates WV. Accordingly, by checking the separated distance between the target substrate WT and the origin, the separated distance between the target substrate WT and the average of the virtual substrates WV can be simply checked.

Further, as can be seen from the histogram 312d, it may be possible to visually check an inter-particle distance at which the difference between the histogram of the target substrate WT and the average histogram of the virtual substrates WT is large. By way of example, as can be seen from the histogram 312d shown in FIG. 9, the histogram of the target substrate WT is positioned over the average histogram of the virtual substrates WV when the inter-particle distance is smaller than or equal to about 500. This indicates that particles having relatively short inter-particle distances are distributed.

Figure 10:
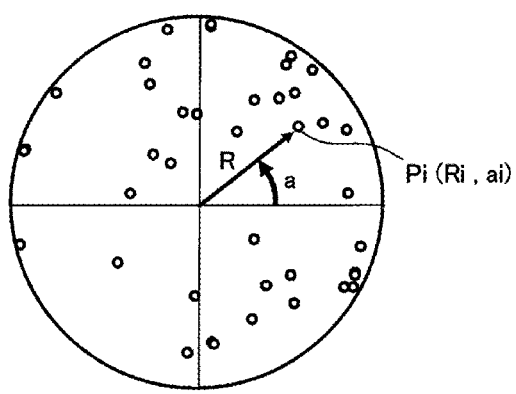
FIG. 10 is a diagram for describing particle coordinate data when particle coordinates are expressed as polar coordinates.
Figure 11:
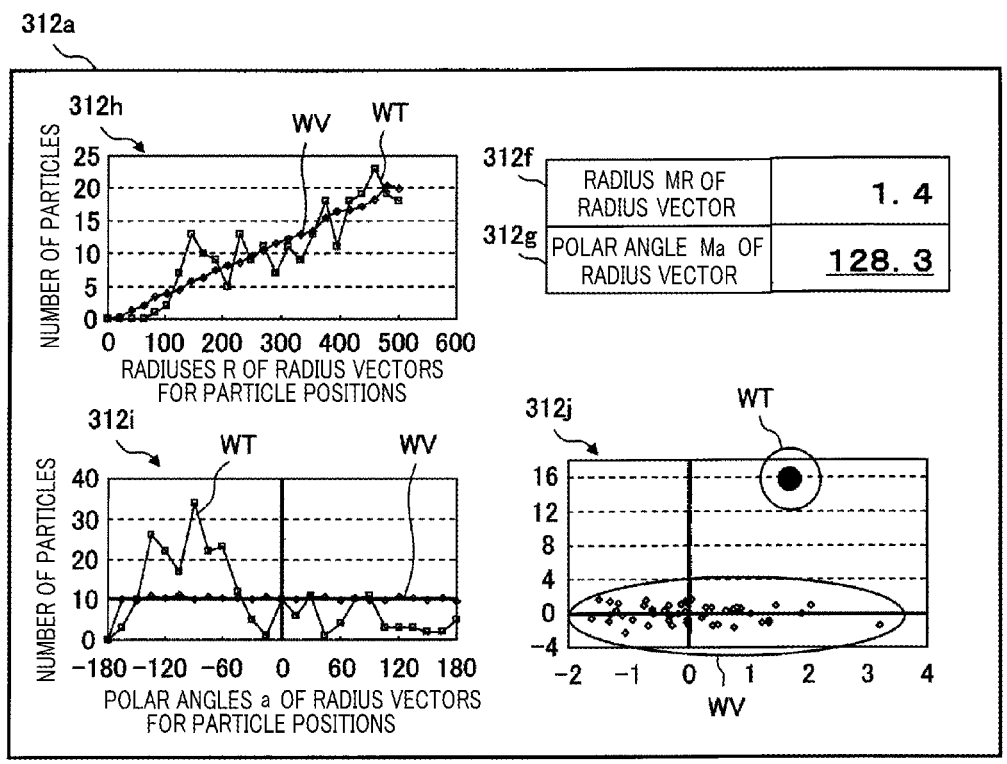
FIG. 11 is a diagram showing an example of displaying an analysis result of radiuses and polar angles of radius vectors for particle positions.

The above analysis example has described the case of using the inter-particle distances as an indicator for the particle distribution characteristics. However, the present disclosure is not limited thereto. By way of example, as shown in FIG. 10, radiuses or polar angles of radius vectors for particle positions may be used as an indicator for the particle distribution characteristics. Here, the radiuses or the polar angles of the radius vectors may be calculated by expressing the particle coordinate data (particle map) as polar coordinates having the center of the substrate as a pole. As in the case of using the inter-particle distances, in the case of using the radiuses and the polar angles of the radius vectors, the histogram data of the target substrate WT and the histogram data of the virtual substrates WV may be generated, and the difference data, the determination data and the display data thereof may also be created. FIG. 11 shows the specific example of the display data displayed on the screen 312a of the display unit 312 in the case of using the radiuses and the polar angles of the radius vectors.

FIG. 11 shows an example of displaying, on the screen 312a, radius determination data 312f and polar angle determination data 312g calculated by the Mahalanobis distance from the difference data, a radius histogram 312h, a polar angle histogram 312i, and a difference map 312j visualizing the difference data. The square root of sum of square of the radiuses of the radius vectors and the square root of sum of square of the polar angles of the radius vectors may be respectively calculated as the difference data of the histograms. On the difference map 312j, a horizontal axis may represent the difference data of the radiuses of the radius vectors and a vertical axis may represent the difference data of the polar angles of the radius vectors, respectively. Here, the difference data may be standardized by the average and the standard deviation of all the virtual substrates WV1 to WVM. Accordingly, the origin of the difference map may be the average, and the standard deviation of the difference map may be about 1.

The display data illustrated in FIG. 11 may be checked in the following manner. First of all, the radius determination data 312f is about 1.4 not exceeding the threshold value, whereas the polar angle determination data 312g is about 128.3 considerably exceeding the threshold value. Accordingly, it may be possible to easily check that the particle distribution is abnormal more in the polar angles of the radius vectors than in the radiuses of the radius vectors.

Moreover, as can be seen from the difference map 312j, the difference data of the target substrate WT is distant from the difference data of the virtual substrates WV. Accordingly, the abnormality of the particle distribution can be easily determined visually. Further, as illustrated in FIG. 11, by standardizing the difference data by the average and the standard deviation of the virtual substrates WV, it may be possible to create the data which is not dependent on the number of particles or the size of the substrate. The calculation method for the standardization will be described in detail later.

Furthermore, as can be seen from the difference map 312j, the horizontal axis represents the radiuses of the radius vectors. Accordingly, when the particles on the target substrate WT are concentrated at the center (direction in which the radiuses of the radius vectors are decreased) compared to the virtual substrates WV each having randomly distributed particles, the difference data of the target substrate WT may be plotted on the left side of the difference map 312j. On the contrary, when the particles on the target substrate WT are concentrated at the periphery (the direction in which the radiuses of the radius vectors are increased), the difference data of the target substrate WT may be plotted on the right side of the difference map 312j. Further, as can be seen from the difference map 312j, the vertical axis represents the polar angles of the radius vectors. Accordingly, when the particles on the target substrate WT are concentrated in a cluster shape at a specific polar angle, the difference data of the target substrate WT may be plotted on the upper side of the difference map 312j. That is, as can be seen from the difference map 312j, the concentration pattern of the particles can be estimated by the plotted positions of the difference data.

Further, as can be seen from the polar angle histogram 312i corresponding to the polar angle determination data 312g having the large value, the difference between the histogram of the target substrate WT and the average histogram of the virtual substrates WV may be largest when the polar angle ranges from about −60° to about −120°. This indicates that the abnormality of the particle distribution is serious within such polar angle range.

These abnormal positions may be visualized on the substrate. That is, with respect to the radiuses and the polar angles of the radius vectors for the particle positions, there may be generated a ranking map in which the polar angles of one or more classes, having a large number difference between the histogram data of the target substrate WT and the average histogram data of the virtual substrates WV1 to WVM in descending order, in each class of the histogram data of the target substrate are displayed on the particle map.

Figure 12:
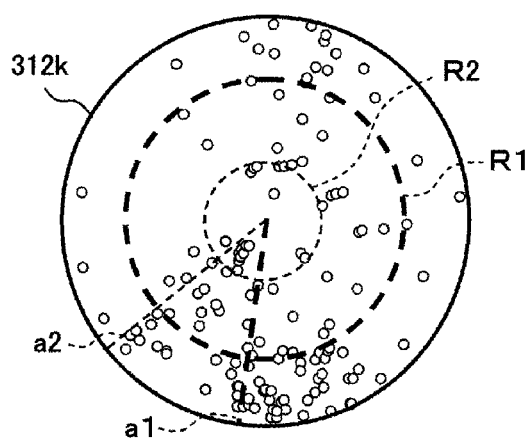
FIG. 12 is a diagram showing a specific example of a ranking map for radiuses and polar angles of radius vectors for particle positions.

FIG. 12 shows an example of a ranking map 312k. On the ranking map 312k, a bold circle (doted lines) R1 and a bold straight line (dotted lines) a1 respectively indicating a radius and a polar angle of a radius vector for a particle position in a class at which the difference in the radius histogram 312h and the polar angle histogram 312i shown in FIG. 11 is the largest may be displayed on the particle map. Further, a circle (dotted lines) R2 and a straight line (dotted lines) a2 respectively indicating a radius and a polar angle of a radius vector for a particle position in a class corresponding to a second largest number difference may also be displayed on the particle map. As can be seen from the ranking map 312k, it may be possible to easily determine the position on the substrate where the particle distribution is abnormal. Further, FIGS. 9 and 11 may be overlapped on a single screen.

(Specific Example of Particle Distribution Analysis Supporting Process)

Figure 13:
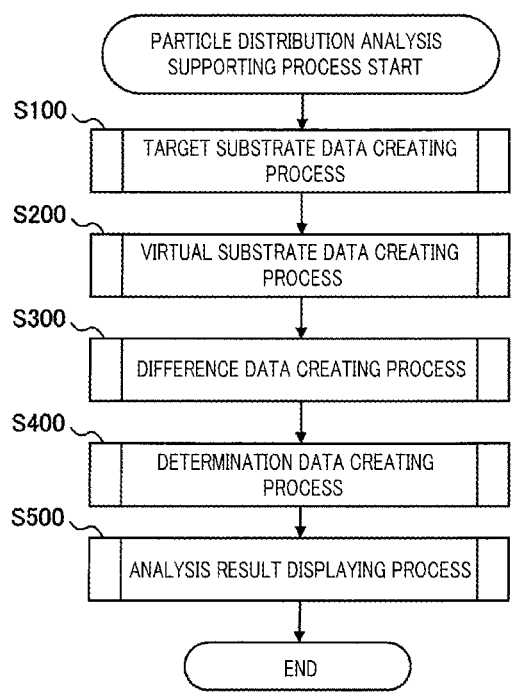
FIG. 13 provides a flowchart showing a main routine of a particle distribution analysis supporting process in accordance with the present embodiment.

Hereinafter, the particle distribution analysis supporting process performed by the particle distribution analysis supporting apparatus 300 will be described with reference to the drawings. FIG. 13 provides a flowchart showing a main routine of the particle distribution analysis supporting process. FIGS. 14 to 18 respectively provide flowcharts showing subroutines of a target substrate data creating process, a virtual substrate data creating process, a difference data creating process, a determination data creating process, an analysis result displaying process shown in FIG. 13.

In order to perform the particle distribution analysis supporting process, the operation processing unit 330 may serve as the target substrate data creating unit 331, the virtual substrate data creating unit 332, the difference data creating unit 333, the determination data creating unit 334, and the display controller 335 based on a program. Further, required data may be stored in the storage unit 320 or may be read out from the storage unit 320 at certain timing.

As for the particle distribution analysis supporting process, there will be described the case of creating three types of histograms, i.e., inter-particle distances, radiuses of radius vectors for particle positions, and polar angles of radius vectors for particle positions for a single target substrate WT and a multiple M-number (e.g., 50) of virtual substrates WV1 to WVM. The difference between the histogram of the target substrate WT and the average histogram of the virtual substrates WV1 to WVM may be determined by creating two types of difference data, i.e., the square root of sum of square and the number of intersection points, for each of the three types of histograms.

The particle distribution analysis supporting process may be performed in the following sequence as shown in FIG. 13. First of all, in process S100, a target substrate data creating process is performed. In the target substrate data creating process, for example, histogram data shown in FIG. 6 may be generated for a single target substrate WT to be subjected to the particle distribution analysis.

Figure 14:
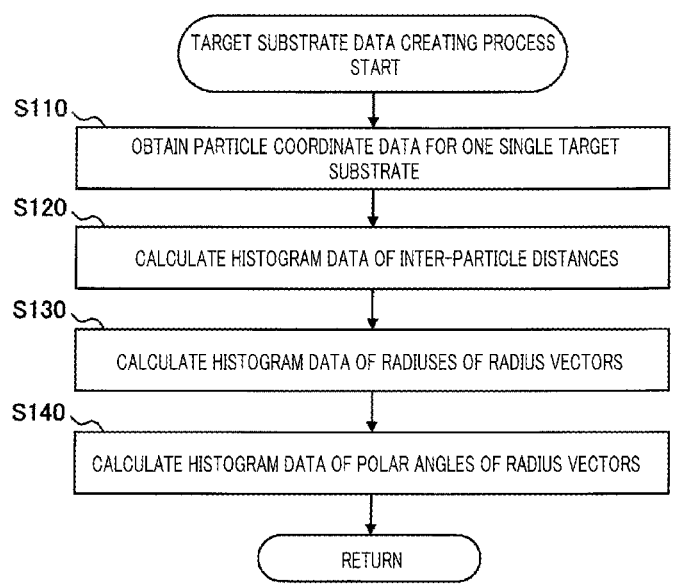
FIG. 14 provides a flowchart showing a specific example of a sub-routine of a target substrate data creating process illustrated in FIG. 13.

Specifically, as illustrated in FIG. 14, in process S110, the particle coordinate data may be obtained from the particle measurement result of the target substrate WT. By way of example, if the particle coordinate data of the target substrate WT to be subjected to the particle distribution analysis is inputted by manipulation of the operator through the input unit 311, the process S120 and subsequent processes may be automatically performed. The particle coordinate data may be obtained by expressing the surface of the substrate as Cartesian coordinates (XY coordinates) as shown in FIG. 4.

The particle coordinate data (particle map) obtained from the measurement result in the particle measurement room 135 of the substrate processing apparatus 100 may be used. Here, the particle distribution analysis supporting apparatus 300 may be connected to the control unit 170 via the network, any may receive the particle coordinate data by communicating with the control unit 170.

Figure 19:
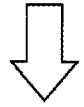
FIG. 19 is a diagram showing examples of inter-particle distances and histogram data of a target substrate.

Thereafter, in process S120, the histogram data of the inter-particle distances may be obtained. Specifically, the inter-particle distances may be calculated from the particle coordinate data by the following equation 1. In the following equation 1, $p_x(i)$ and $p_y(i)$ respectively denote an X coordinate and an Y coordinate of an i-th particle Pi; and $p_x(j)$ and $p_y(j)$ respectively denote an X coordinate and an Y coordinate of a j-th particle Pj. $d_{ij}$ denotes a distance between the particle Pi and the particle Pj. Since $d_{ii}$ denotes the particle Pi itself, the distance is zero. The inter-particle distances are shown in FIG. 19. FIG. 19 shows the inter-particle distances between each of particles P1 to PN and other particles when the number of particles is N.

[Equation 1]

$$d_{ij} = \sqrt{((p_x(i)-p_x(j))^2 + (p_y(i)-p_y(j))^2} \quad (1)$$

Then, the histogram of the inter-particle distances may be generated. Specifically, the inter-particle distances may be classified into a multiple number of (e.g., 1000) classes, and the number of particles in each of the multiple number of classes may be calculated. Thus, the histogram of the inter-particle distances may be generated. A specific example of the histogram data is illustrated in FIG. 19. In the histogram data illustrated in FIG. 19, d denotes classes ranging from 0 to D. By way of example, when the inter-particle distances are classified into, e.g., 1000 classes, D may be 1000. Further, Fc(d) denotes a frequency of the class d. In this way, the histogram of the target substrate WT shown in FIG. 6 may be generated.

Next, in process S130, the histogram data of the radiuses of the radius vectors for the particle positions may be generated. Specifically, the Cartesian coordinates (XY coordinates) may be converted to the polar coordinates having the center of the target substrate WT as the pole. Thereafter, the radiuses R of the radius vectors for the particle positions on the polar coordinates may be classified into a multiple number of classes, i.e., r=0 to D/2, and the number of particles in each class may be calculated. Thus, the histogram of the radiuses of the radius vectors may be generated.

Thereafter, in process S140, the histogram data of the polar angles of the radius vectors for the particle positions may be obtained. Specifically, the polar angles a of the radius vectors for the particle positions on the polar coordinates may be classified into a multiple number of classes, i.e., θ=−180°∼+180°, and the number of particles in each class may be calculated. Thus, the histogram of the polar angles of the radius vectors may be generated. In this way, three types of histogram data may be g for the single target substrate WT.

Next, the process proceeds to a virtual substrate data creating process in process S200 of the main routine shown in FIG. 13. In the virtual substrate data creating process, by way of example, the histogram data shown in FIG. 7 may be generated for the M-number (e.g., 50) of virtual substrates each having the same number of randomly distributed particles as the particles on the target substrate WT.

Figure 15:
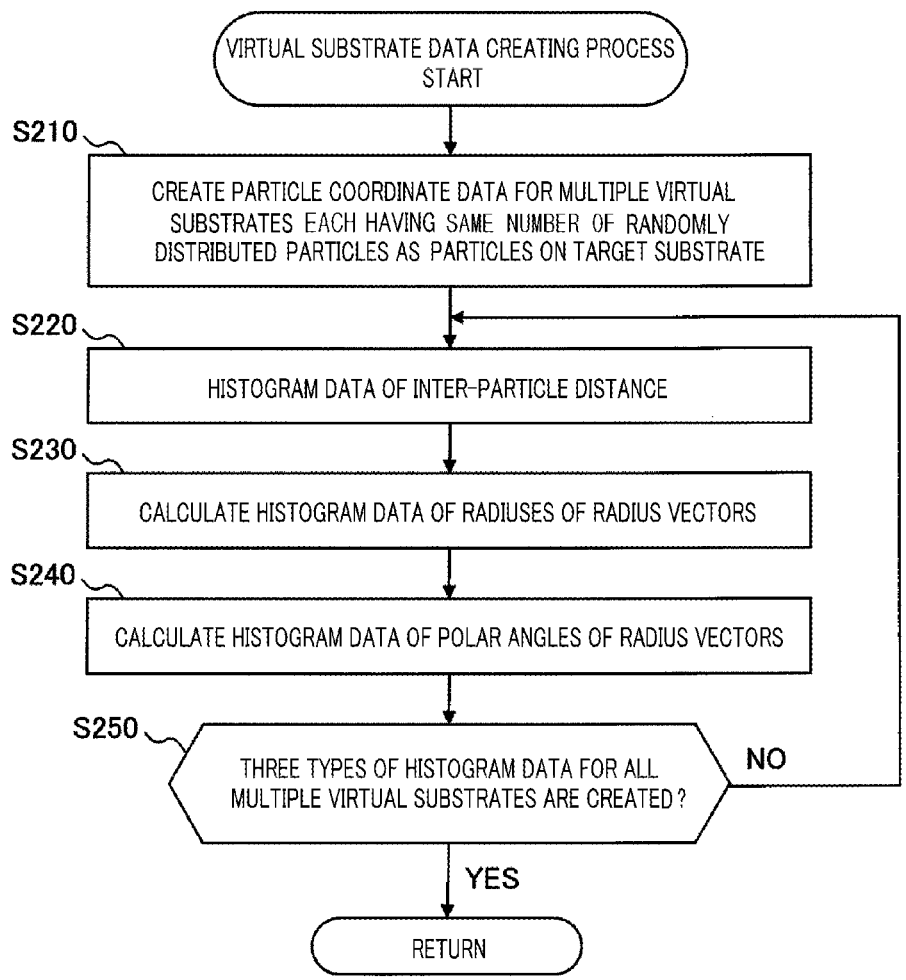
FIG. 15 provides a flowchart showing a specific example of a sub-routine of a virtual substrate data creating process illustrated in FIG. 13.

Specifically, as illustrated in FIG. 15, in process S210, the particle coordinate data on each of the M-number of virtual substrates WV1 to WVM may be created. As in the case of the target substrate, the particle coordinate data may be coordinate data of each particle obtained by expressing the surface of the substrate as Cartesian coordinates (XY coordinated) as shown in FIG. 4

Then, in process S220, the histogram data of the inter-particle distances may be obtained. Specifically, as in the process S210, the inter-particle distances may be calculated from the particle coordinate data by the equation 1. The inter-particle distances are shown in FIG. 20.

Thereafter, the histogram of the inter-particle distances may be generated. Specifically, the inter-particle distances may be classified into a multiple number of (e.g., 1000) classes, and the number (frequency) of particles in each of the multiple number of classes may be calculated. Thus, the histogram the inter-particle distances may be generated. A specific example of the histogram data is illustrated in FIG. 20. In the histogram data shown in FIG. 20, d denotes classes ranging from 0 to D. When the inter-particle distances are classified into, e.g., 1000, classes, D may be 1000. Further, F'cm(d) denotes the number of particles in the class d for the m-th virtual substrate WVm. In this way, the histograms of the virtual substrates WV1 to WVM shown in FIG. 7 may be generated.

Then, in process S230, the histogram data of the radiuses of the radius vectors for the particle positions may be obtained. Specifically, the Cartesian coordinates (XY coordinates) may be converted to the polar coordinates having the center of each of the target substrates WV as the pole. Thereafter, the radiuses R of the radius vectors for the particle positions on the polar coordinates may be classified into a multiple number of classes, i.e., r=0 to D/2, and the number of particles in each class may be calculated. Thus, the histogram of the radiuses of the radius vectors may be generated.

Next, in process S240, the histogram data of the polar angles of the radius vectors for the particle positions may be obtained. Specifically, the polar angles a of the radius vectors for the particle positions on the polar coordinates may be classified into a multiple number of classes, i.e., θ=−180°∼+180°, and the number of particles in each class may be calculated. Thus, the histogram of the polar angles of the radius vectors may be generated. In process S250, it may be determined whether or not the histogram data is generated for all of the virtual substrates. When the histogram data is determined not to be created for all of the virtual substrates, the processes S220 to S240 may be repeated until the histogram data is generated for all of the virtual substrates. In this way, three types of histogram data may be generated for each of the M-number of virtual substrates WV1 to WVM.

Thereafter, the process proceeds to a difference data creating process in process S300 of the main routine shown in FIG. 13. In the difference data creating process, the difference data indicating the difference between the histogram data of the target substrate WT and the histogram data of the virtual substrates WV1 to WVM may be created. As the difference data, the square root of sum of square and the number of intersection points may be calculated. Further, after each histogram data is standardized, the difference data may be created from the standardized histogram data.

Figure 16:
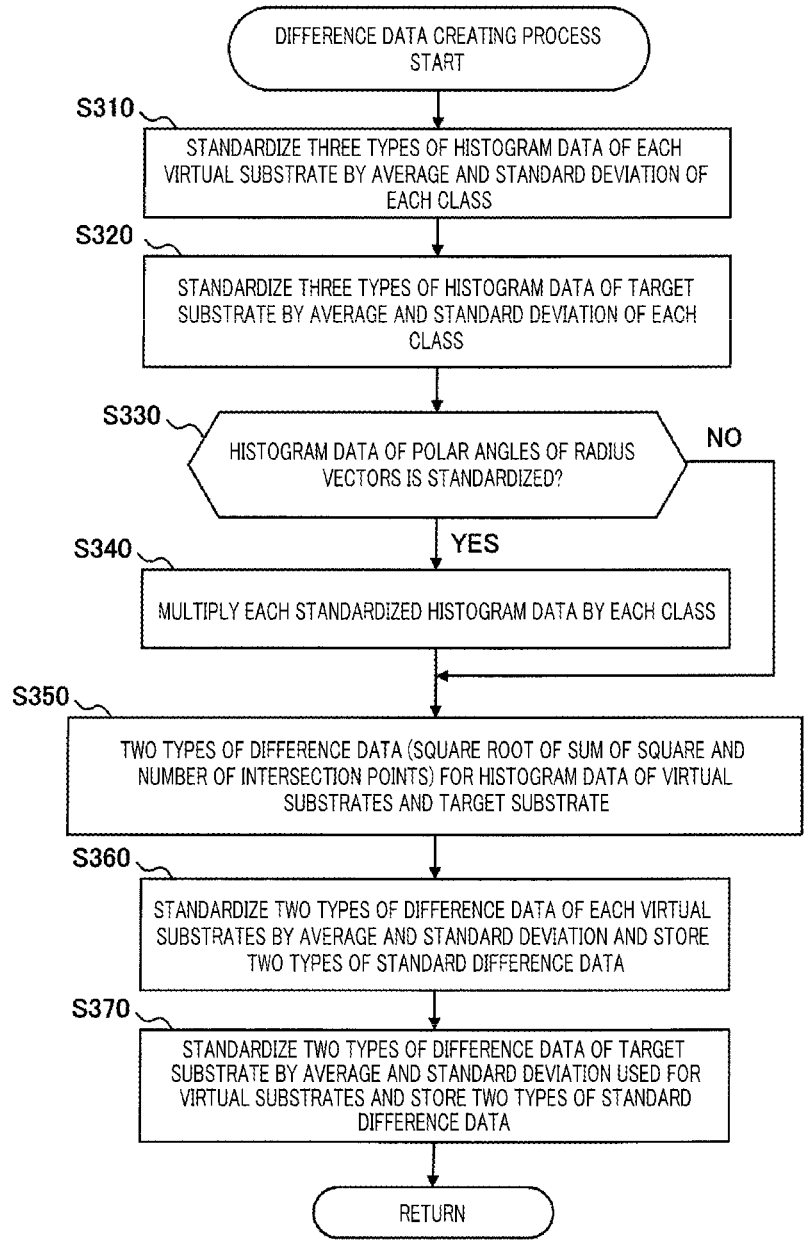
FIG. 16 provides a flowchart showing a specific example of a sub-routine of a difference data creating process illustrated in FIG. 13.

Specifically, as shown in FIG. 16, in process S310, three types of histogram data (the inter-particle distances, and the radiuses and the polar angles of the radius vectors) of the M-number of virtual substrates WV1 to WVM may be standardized by the average and the standard deviation of each class. Here, the average and the standard deviation may be obtained from the histogram data of the virtual substrates WV1 to WVM. By way of example, the average $F_c'(d)$ and the standard deviation $\sigma F_c'(d)$ may be calculated by the following equation 2, and the histogram data of the inter-particle distances may be standardized by the following equation 3 by using the average $F_c'(d)$ and the standard deviation $\sigma F_c'(d)$. The standardized histogram data of the inter-particle distances is shown in FIG. 21. The histogram data of the radiuses and the polar angles of the radius vectors for the particle positions may be also standardized.

[Equation 2]

$$\langle F_c'(d) \rangle \equiv \frac{1}{M} \sum_{m=1}^{M} F_{cm}'(d) \qquad (2)$$

$$\sigma_{F_c'}(d) \equiv \sqrt{\frac{1}{M} \sum_{m=1}^{M} (F_{cm}'(d))^2 - (\langle F_c'(d) \rangle)^2}$$

[Equation 3]

$$\overline{F_{cm}'(d)} = \frac{F_{cm}'(d) - \langle F_c'(d) \rangle}{\sigma_{F_c'}(d)} \qquad (3)$$

Next, in process S320, the three types of histogram data (the inter-particle distances, and the radiuses and the polar angles of the radius vectors) of the target substrate WT may be standardized. Here, the three types of histogram data may be standardized by the average and the standard deviation used for the virtual substrates WV. By way of example, the average $F_c'(d)$ and the standard deviation $\sigma F_c'(d)$ may be calculated by the equation 2, and the histogram data of the inter-particle distances may be standardized by the equation 3 by using the average $F_c'(d)$ and the standard deviation $\sigma F_c'(d)$. The standardized histogram data of the inter-particle distances is illustrated in FIG. 21. The histogram data of the radiuses and the polar angles of the radius vectors for the particle positions may be also standardized.

Next, in process S330, it may be determined whether or not the radiuses of the radius vectors for the particle positions are calculated. When it is determined in the process S330 that the radiuses of the radius vectors for the particle positions are not calculated, i.e., when the inter-particle distances or the polar angles of the radius vectors are calculated, the process proceeds to the process S350. Meanwhile, when it is determined in the process S330 that the radiuses of the radius vectors for the particle positions are calculated, the standardized histogram data may be additionally generated in the process S340 by multiplying histogram data of the target substrate WT and the virtual substrates WV1 to WVM by each class (the radius of the radius vector). Thereafter, the process proceeds to process S350.

As described above, only for the histogram of the radiuses of the radius vectors, the standardized histogram is additionally generated by multiplying the standardized histogram data by each class (the radius of the radius vector). This is because that it is possible to easily determine whether the particle distribution is concentrated at the center of the substrate or at the periphery thereof in the radial direction, as can be seen from the difference map 312j of the radiuses and the polar angles of the radius vectors for on the particle positions shown in FIG. 11 and FIG. 27 to be described later. That is, since the standardized histogram has dimensionless value, it may be difficult to determine the concentrated direction of the particle distribution. Therefore, by multiplying the standardized histogram by each class, the standardized histogram may have the dimension of the distance from the center of the substrate to the periphery thereof. By way of example, as indicated in the horizontal axis of FIG. 27, the difference data may be plotted on the right side from zero as the particle distribution is concentrated at the periphery of the substrate, whereas the difference data may be plotted on the left side from the zero as the particle distribution is concentrated at the center of the substrate. Accordingly, it may be possible to determine whether the particle distribution is concentrated at the center of the substrate or the periphery thereof by the plotted position of the difference data.

Meanwhile, as for the histogram of the polar angles of the radius vectors, the standardized histogram is not multiplied by each class (the polar angle of the radius vector). This is because the polar angles of the radius vectors revolve on the substrate by about 360°, and it may be difficult to determine the particle distribution in the polar angles of the radius vectors when the standardized histogram data is multiplied by each class. By way of example, the polar angle of the radius vector obtained when the difference data is plotted near about −180° and the polar angle of the radius vector obtained when the difference data is plotted near about +180° may be substantially the same. Accordingly, the difference data of about +180° and the difference data of about −180° need to be plotted at the same position. However, if the standardized histogram data of the polar angles of the radius vectors is multiplied by each class, these difference data of about +180° and −180° may be plotted at positions opposite to each other on the difference map 312j. Therefore, it may be difficult to accurately determine the non-uniform of the particle distribution in the polar angles of the radius vectors. For this reason, as for the polar angles of the radius vectors, the standardized histogram data may be not multiplied by each class. Further, the detailed description of the difference map 312j illustrated in FIG. 27 will be provided later.

Next, in process S350, 'the square root of sum of square of the particle number' and 'the number of intersection points of the particle number' may be obtained for three types of the standardized histogram data (inter-particle distances, radiuses of radius vectors, and polar angles of radius vectors) of the virtual substrates WV1 to WVM and the target substrate WT. Since the standardized histogram data has been standardized by the average and the standard deviation of the histogram data of the virtual substrates, 'the square root of sum of square of the particle number' of each histogram data may serve as the data (difference data) indicating the difference between the corresponding histogram data and the average histogram data of the virtual substrates. Moreover, 'the number of intersection points of the particle number' of each histogram data may indicate the number of intersection points between the corresponding histogram data and the average histogram data of the virtual substrates. Accordingly, 'the number of intersection points of the particle number' may serve as the data (difference data) indicating the difference between the corresponding histogram data and the average histogram data of the virtual substrates.

By way of example, 'the square root of sum of square of the particle number' of the inter-particle distances may be calculated by the following equation 4. Further, 'the number of intersection points of the particle number' may be calculated by counting the number of intersection points. The difference data of the inter-particle distances are shown in FIG. 21.

[Equation 4]

$$[F'_{cm}] \equiv \sqrt{\sum_{d=0}^{D}(F'_{cm}(d))^2} \quad (4)$$

Thereafter, in process S360, 'the square root of sum of square of the particle number' and 'the number of intersection points of the particle number' serving as the difference data of the virtual substrates WV1 to WVM may be standardized by the average and standard deviation thereof. Next, in process S370, 'the square root of sum of square of the particle number' and 'the number of intersection points of the particle number' serving as the difference data of the target substrate WT may be standardized by the average and the standard deviation used for the virtual substrates. The standardized difference data may be stored in the data storage unit 322.

FIGS. 22A to 22C illustrate the standardized difference data of the inter-particle distances, the radiuses of the radius vectors for the particle positions, and the polar angles of the radius vectors for the particle positions, respectively, calculated by the above-mentioned method. In this way, two standardized difference data, i.e., 'the square root of sum of square of the particle number' and 'the number of intersection points of the particle number', of each of the three types of indicators, i.e., the inter-particle distances, the radiuses of the radius vectors for the particle positions, and the polar angles of the radius vectors for the particle positions may be created for the single target substrate WT and the M-number of virtual substrates WV1 to WVM.

Then, the process proceeds to a determination data creating process in process S400 of the main routine shown in FIG. 13. In the determination data creating process, the difference between the target substrate WT and the virtual substrates WV1 to WVM may be quantified by a statistical method while using the standardized difference data created by the difference data creating process. Here, the Mahalanobis distance may be used as the statistical method.

Figure 17:
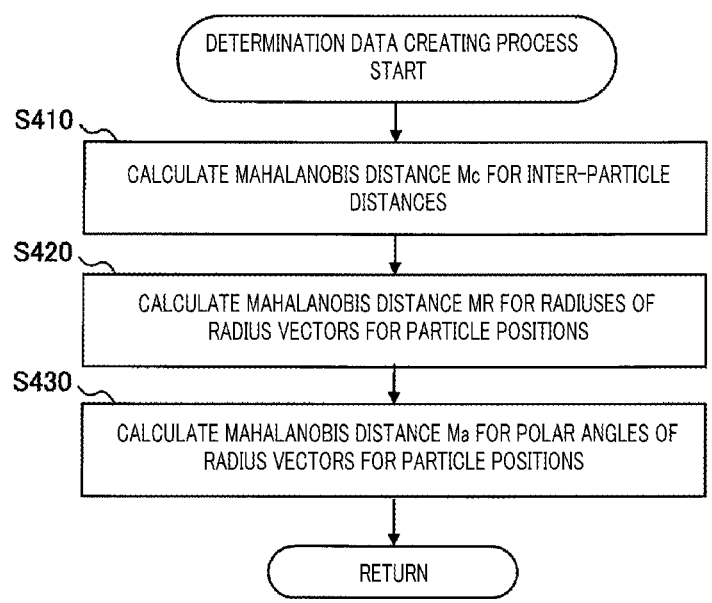
FIG. 17 provides a flowchart showing a specific example of a sub-routine of a determination data creating process illustrated in FIG. 13.

Specifically, as illustrated in FIG. 17, in process S410, the Mahalanobis distance Mc of the inter-particle distances may be calculated. The correlation matrix Φ may be obtained by the following equation 5 by using two types of the standardized difference data (the square root of sum of square and the number of intersection points) of the virtual substrates WV1 to WVM shown in FIG. 22A. The Mahalanobis distance of the target substrate WT may be calculated by the following equation 6 by using the correlation matrix Φ. Thereafter, Mahalanobis distance of the target substrate WT may be stored in the data storage unit 322.

[Equation 5]

$$\Phi' \equiv \begin{pmatrix} a & b \\ c & d \end{pmatrix} \begin{cases} a = d = 1 \\ b = c = \dfrac{1}{M-1}\left(\sum_{m=1}^{M} \overline{[F'_{cm}]} \cdot \overline{[[F'_{cm}]]}\right) \end{cases} \quad (5)$$

$$\Phi = \Phi'^{-1}$$

$$= \frac{1}{ad-bc}\begin{pmatrix} d & -b \\ -c & a \end{pmatrix} \equiv \begin{pmatrix} \alpha & \beta \\ \gamma & \eta \end{pmatrix}$$

[Equation 6]

$$M_c = \frac{1}{2}(\overline{[F_c]} \quad \overline{[[F_c]]})\begin{pmatrix} \alpha & \beta \\ \gamma & \eta \end{pmatrix}\begin{pmatrix} \overline{[F_c]} \\ \overline{[[F_c]]} \end{pmatrix} \quad (6)$$

Next, in process S420, the Mahalanobis distance MR of the radiuses of the radius vectors for the particle positions may be calculated. In process S430, the Mahalanobis distance Ma of the polar angles of the radius vectors for the particle positions may be calculated. In processes S420 and S430, as in process S410, the correlation matrix Φ ($p_i$) may be obtained by using two types of the standardized difference data (the square root of sum of square, the number of intersection points) of the virtual substrates WV1 to WVM shown in FIGS. 22B and 22C. The Mahalanobis distances MR and Ma of the target substrate WT may be calculated by using the correlation matrix (0). Thereafter, the Mahalanobis distances MR and Ma of the target substrate WT may be stored in the data storage unit 322.

Figure 18:
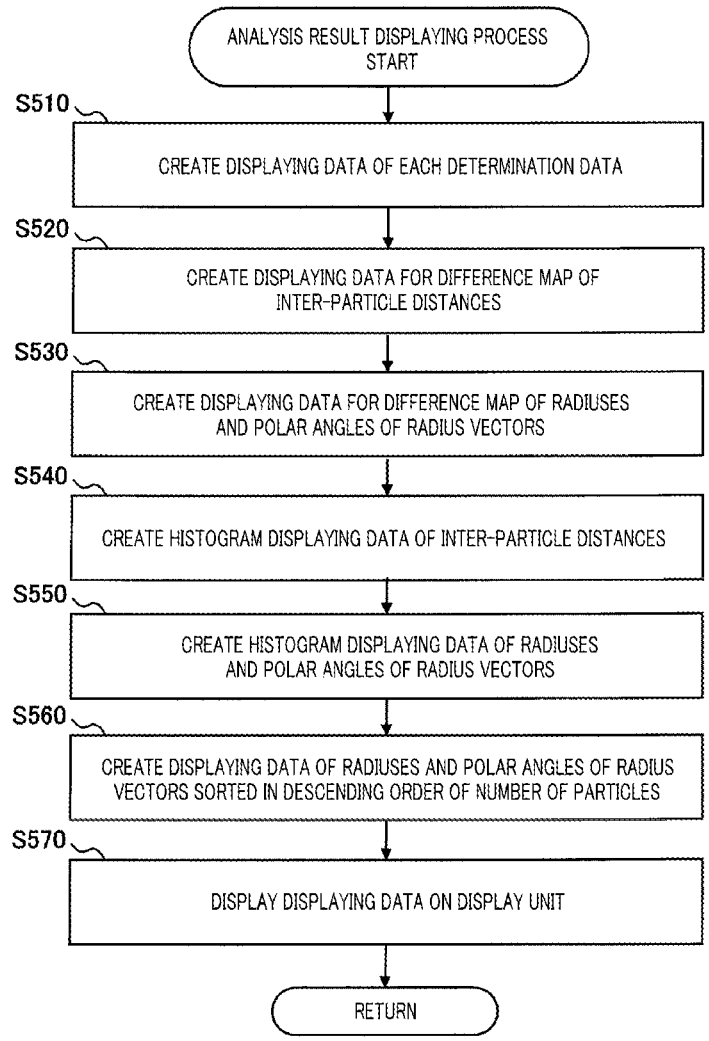
FIG. 18 provides a flowchart showing a specific example of a sub-routine of an analysis result displaying process illustrated in FIG. 13.
Figure 23:
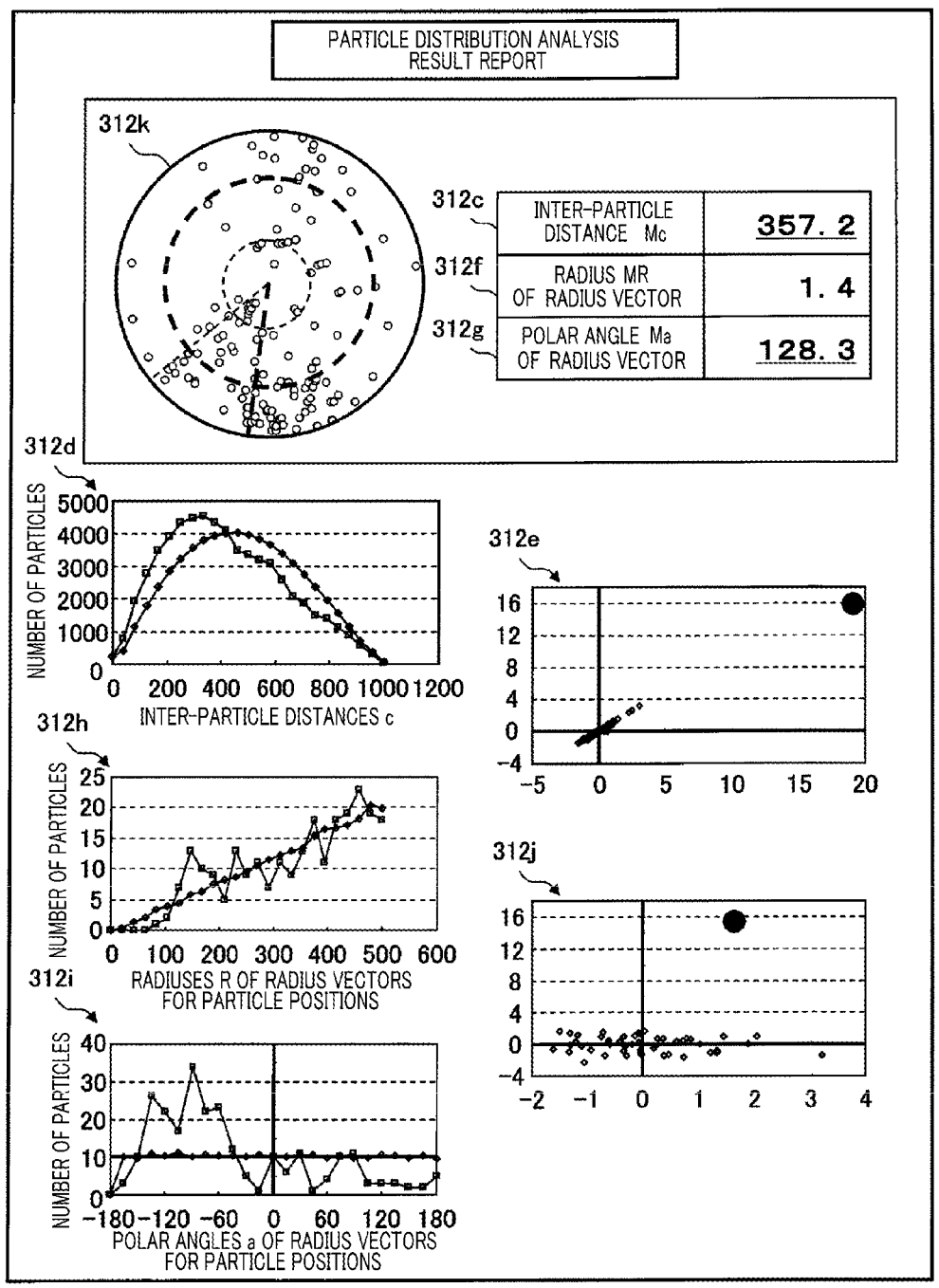
FIG. 23 is a diagram showing another example of displaying a particle distribution analysis result.

Thereafter, the process proceeds to an analysis result displaying process in process S500 of the main routine shown in FIG. 13. In the analysis result displaying process, display data for displaying the Mahalanobis distances Mc, MR, and Ma serving as the determination data may be created in process S510 as shown in FIG. 18. In this case, the determination data may be displayed separately as shown in FIGS. 9 and 11. Alternatively, the determination data may be displayed all together as shown in FIG. 23. FIG. 23 shows an example of displaying, on one screen, the determination data, the difference map and the histogram illustrated in FIGS. 9 and 11 all together.

Then, in process S520, the display data of the difference map 312e of the inter-particle distances shown in FIGS. 9 and 23 may be created. Specifically, the square root of sum of square and the number of intersection points of the standardized difference data shown in FIG. 22A may be represented on the horizontal axis and the vertical axis, respectively. Then, the corresponding data of the target substrate WT and the virtual substrates WV1 to WVM may be plotted.

Thereafter, in process S530, the display data of the difference map 312j shown in FIGS. 11 and 23 may be created for the radiuses and the polar angles of the radius vectors for the particle positions. Specifically, the square root of sum of square of the radiuses of the radius vectors shown in FIG. 22B and the square root of sum of square of polar angles of the radius vectors shown in FIG. 22C may be represented on the horizontal axis and the vertical axis, respectively. Then, the corresponding data of the target substrate WT and the virtual substrates WV1 to WVM may be plotted.

Next, in process S540, the display data of the histogram 312d shown in FIGS. 9 and 23 may be created for the inter-particle distances. Specifically, the histogram data of the target substrate WT shown in FIG. 19 and the average histogram data of the virtual substrates WV1 to WVM shown in FIG. 20 may be used as the display data. The average histogram data of the virtual substrates WV1 to WVM may be obtained by averaging the histogram data in each class thereof.

Thereafter, in process S550, the display data of the histograms 312h and 312i of the radiuses and the polar angles of the radius vectors for the particle positions shown in FIGS. 11 and 23 may be created. Specifically, as in the case of creating the display data of the inter-particle distances, the histogram data of the radiuses and the polar angles of the radius vectors for the particle positions on the target substrate WT and the average histogram data of the radiuses and the polar angles of the radius vectors for the particle positions on the virtual substrates WV1 to WVM may be used as the display data. The average histogram data of the virtual substrates WV1 to WVM may be obtained by averaging the histogram data in each class thereof.

Thereafter, in process S560, the display data of the ranking map 312k shown in FIGS. 12 and 23 may be created. Specifically, with respect to the histograms 312h and 312i of the radiuses and the polar angles of the radius vectors for the particle positions, the classes may be sorted in descending order of frequency (number). Thereafter, with respect to a predetermined number of high rank classes, straight lines indicating the radiuses of the radius vectors and circles indicating the polar angles of the radius vectors may be overlapped on the map.

Next, in process S570, the determination data 312c, 312f and 312g, the difference maps 312e and 312j and the ranking map 312k which are generated in the processes S510 to S560 may be displayed, as the particle distribution analysis result report, on the screen of the display unit 312, as illustrated in FIG. 23, for example. Further, when the determination data is greater than or equal to the certain threshold value (about 4 in this example), it may be desirable to highlight the determination data (underline in this example). Accordingly, it may be possible to easily determine whether or not the abnormality is generated. Upon completion of the analysis result displaying process shown in FIG. 18, the process may return to the main routine of FIG. 13. A series of the particle distribution analysis supporting process may be completed.

In accordance with this particle distribution analysis supporting process, when the operator inputs the particle coordinate data of the target substrate to be subjected to the particle distribution analysis through the input unit 311, the processes illustrated in FIG. 13 may be automatically carried out and, then, the final particle distribution analysis result report may be displayed on the display unit 312. As a consequence, the operator can easily determine the abnormality of the particle distribution by checking the report, and the operator can also specify the abnormality by checking the report. Furthermore, the final report can be printed out by manipulation of the operator through the input unit 311.

Figure 24A:
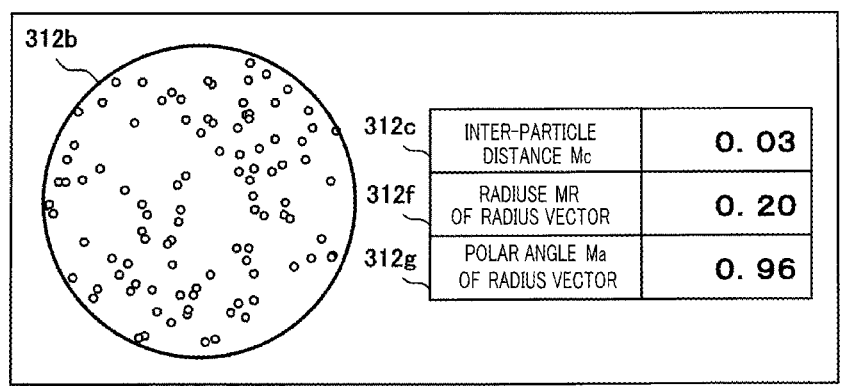
FIG. 24A is a diagram showing a specific example of a particle distribution analysis result for describing a specific example of determination data when there is no abnormality.
Figure 24B:
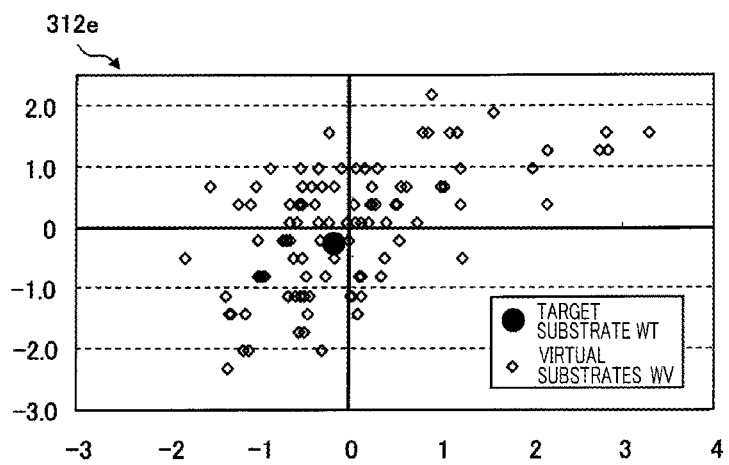
FIG. 24B is a diagram showing a difference map for the example of FIG. 24A.

Hereinafter, another specific example of the analysis result obtained by the particle distribution analysis supporting processes will be described with reference to the drawings. Here, a case where it is difficult to determine the abnormality of the particle map at a glance will be explained for comparison. FIGS. 24A and 24B show the case where the particle distribution is normal. FIGS. 25A to 25D show the case where the particle distribution is abnormal.

Figure 25A:
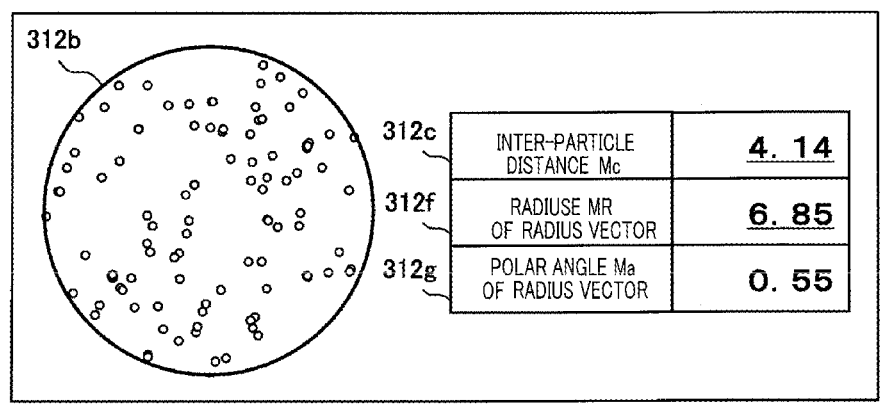
FIG. 25A is a diagram showing a specific example of a particle distribution analysis result for describing a specific example of determination data when there is an abnormality.
Figure 25B:
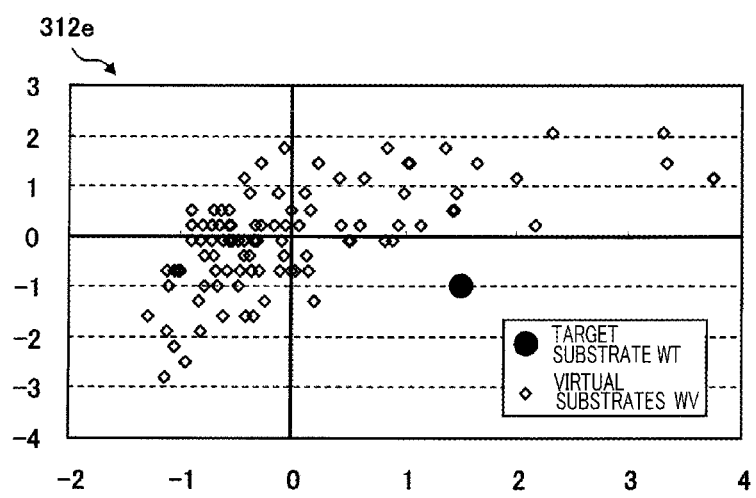
FIG. 25B is a diagram showing a difference map for the example of FIG. 25A.

FIGS. 24A and 25A illustrate the particle map 312b and the determination data Mc, MR and Ma in the particle distribution analysis result report. FIGS. 24B and 25B illustrate the difference map 312e in the particle distribution analysis result report.

In accordance with this analysis result, when the particle maps 312b shown in FIGS. 24A and 25A are compared, it may be difficult to check the difference therebetween. Meanwhile, when the determination data Mc and MR shown in FIGS. 24A and 25A are compared, it is seen that the determination data Mc and MR of FIG. 24A, i.e., 0.03 and 0.20, are considerably smaller than the threshold value, i.e., 4, whereas the determination data Mc and MR of FIG. 25A, i.e., 4.14 and 6.85, are greater than the threshold value, i.e., 4. Therefore, it may be possible to easily check that the particle distribution shown in FIG. 24A is normal and that the particle distribution shown in FIG. 25A is abnormal.

Moreover, when the difference maps 312e shown in FIGS. 24B and 25B are compared, it may be possible to check that the standardized difference data of the target substrate WT in FIG. 24B is close to the center (origin) of the map which indicates the average of the standardized difference data of the virtual substrates WV. Further, it may be possible to check that the standardized difference data of the target substrate WT in FIG. 25B is deviated from the center toward the lower right side. As can be seen from this difference map 312e, as the standardized difference data of the target substrate become distant from the center of the map, the difference between the target substrate and the virtual substrates each having randomly distributed particles may become increased. Therefore, it may be possible to easily determine that the particle distribution shown in FIG. 24B is normal and that the particle distribution shown in FIG. 25B is abnormal.

Figure 25C:
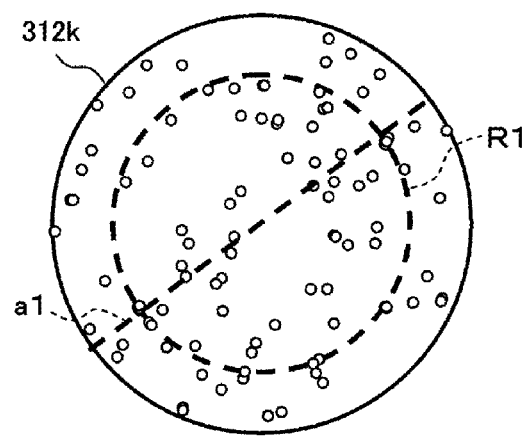
FIG. 25C is a diagram showing a ranking map for the example of FIG. 25A.
Figure 25D:
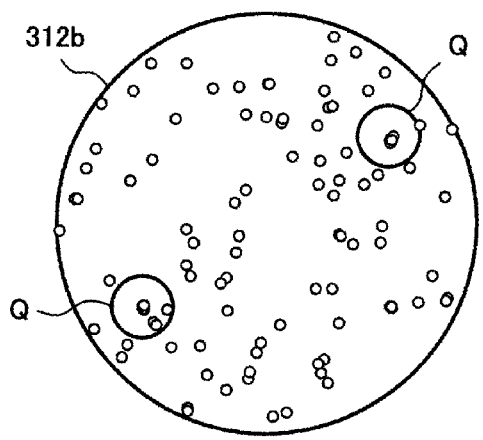
FIG. 25D is a diagram showing abnormal particles distribution checked by the ranking map of FIG. 25C.

When the abnormality is determined as shown in FIGS. 25A and 25B, the ranking map 312k shown in FIG. 25C may be additionally generated. Here, the ranking map 312k may be displayed radius of the radius vector having the largest difference and the polar angle of the radius vector having the largest difference in the histogram of the target substrate WT and the average histogram of the virtual substrate WV with the particle map 312b shown as FIG. 25A. Accordingly, it may be possible to check that the abnormality exists at the intersection points between the circle (dotted lines) R1 indicating the radius of the radius vector having the largest difference and the straight line (dotted line) a1 indicating the polar angle of the radius vector having the largest difference. The intersection points may correspond to positions Q on the particle map shown in FIG. 25D. In FIG. 25D, the positions Q indicating the abnormal positions are displayed on the particle map 312b of FIG. 25A. This indicates that cluster-shaped particles as the main cause of abnormality are concentrated at the positions Q. That is, the positions causing abnormality can be easily specified on the ranking map 312k.

In accordance with the particle distribution analysis process of the present embodiment, even when it is difficult to check the particle distribution at a glance, it may be possible to easily analyze the particle distribution. As a result, the abnormality of the particle distribution can be easily determined even by a non-expert operator.

Besides, as can be seen from the difference map 312j of the radiuses and the polar angles of the radius vectors for the particle positions, the particle distribution characteristics can be classified into some patterns. Here, as shown in FIG. 26, a multiple number of target substrates WT having four characteristic particle distribution patterns may be provided, and the difference map 312j obtained by performing the particle distribution analysis process on the multiple number of target substrates WT is shown in FIG. 27.

Figure 26:
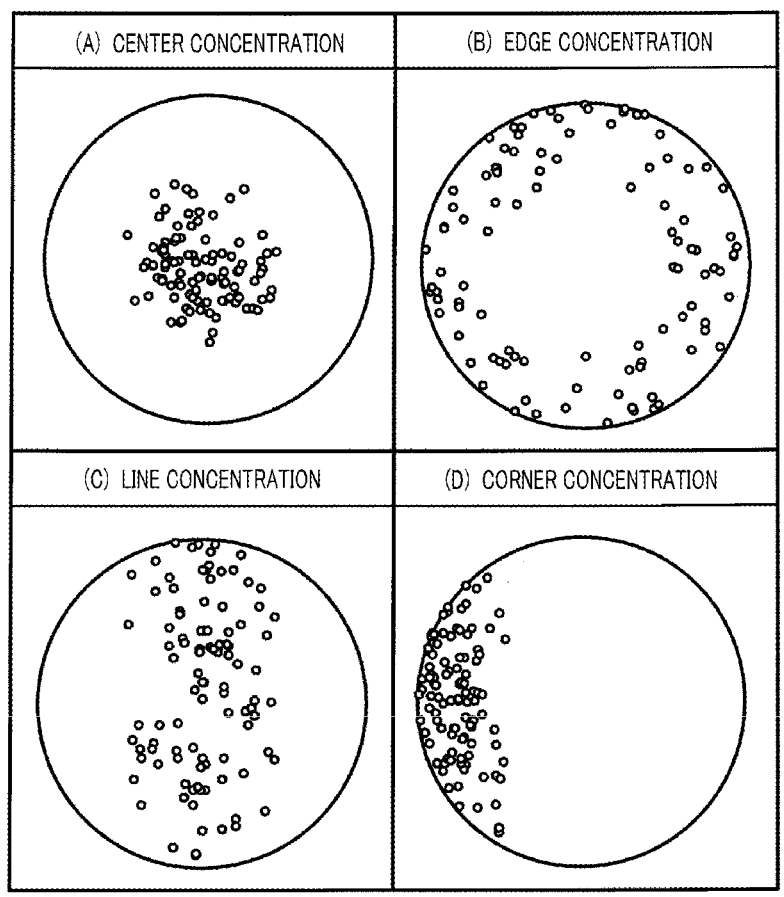
FIG. 26 is a diagram showing four unusual particle distribution patterns.

Among the particle distribution patterns shown in FIG. 26, (A) center concentration shows the case where the particles are concentrated at the center of the substrate; (B) edge concentration shows the case where the particles are concentrated at the edge of the substrate; (C) line concentration shows the case where the particles are concentrated along a straight line in one direction of the substrate; and (D) corner concentration shows the case where the particles are concentrated at one corner of the substrate.

Figure 27:
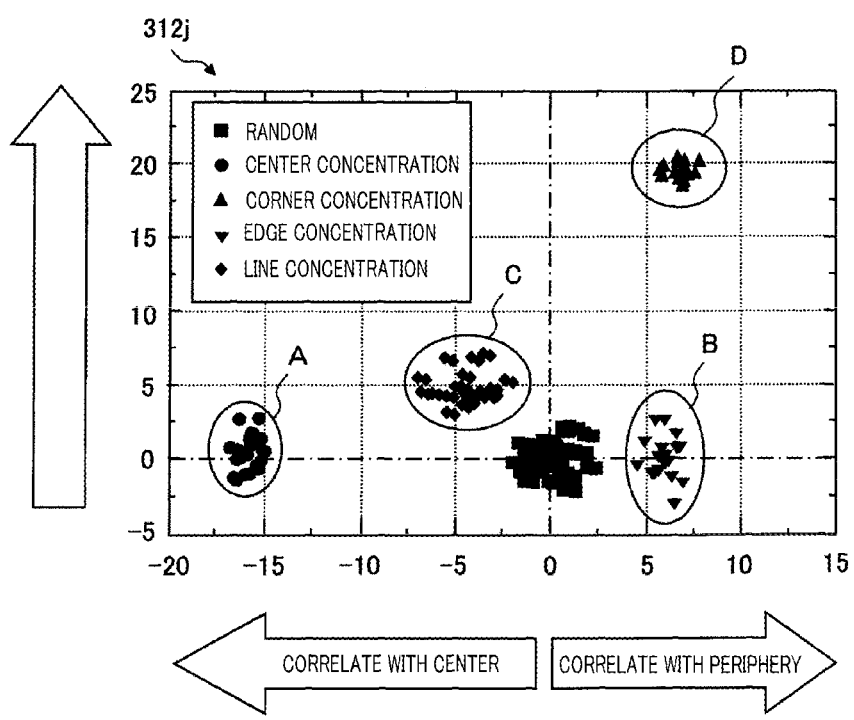
FIG. 27 is a diagram showing a difference map for the distribution patterns of FIG. 26.

As shown in FIG. 27, as can be seen from the difference map 312$j$ of the target substrate WT shown in FIG. 26, the particles are concentrated at specific positions in each of the respective distribution patterns. In FIG. 27, the vertical axis representing the polar angles of the radius vectors may be correlated with the polar angles of the radius vectors. Further, the horizontal axis representing the radiuses of the radius vectors may be correlated with the periphery of the substrate in the plus region and the center thereof in the minus region.

Thus, the particle distribution pattern can be estimated by plotting, on the difference map 312$j$, the standardized difference data of the radiuses and the polar angles of the target substrate WT to be analyzed, for example. By way of example, the particle distribution pattern can be estimated depending on whether the plotted data of the target substrate WT are close the certain particle distribution patterns (A) to (D).

As can be seen from difference map 312$j$, it may be possible to easily determine whether or not the particle distribution is non-uniform, especially, whether the particle distribution is concentrated at the center or the periphery of the substrate. The standardized histogram data used in the present embodiment may represent the deviation from the virtual substrates. Since, however, the standardized histogram data has been standardized by the average and the standard deviation of the virtual substrates, the standardized histogram data has dimensionless value. Here, in the case of using the standardized histogram data that are not multiplied by each class (the inter-particle distance, or the polar angle of the radius vector for the particle position), the difference data become increased as the separated distance from the virtual substrates becomes increased. Since, however, the difference data have dimensionless value, it may be not possible to check the polar angle direction of the difference data.

Meanwhile, whether the radiuses of the radius vectors for the particle positions are concentrated at the center of the substrate or the periphery thereof may be important information. For this reason, the standardized histogram with the dimension of 'distance' can be obtained by multiplying the standardized histogram by each class (distance of radius of radius vector).

By way of example, when the substrate has a diameter of about 1000, the average position of the virtual substrates in the radiuses of the radius vectors is accurately between the periphery of the substrate and the center thereof (radius=500). However, in the distribution pattern concentrated at the center, the histogram data of small classes (center) may have large values, whereas the histogram data of large classes (outer periphery) may have small values. Accordingly, it may be possible to output a smaller value than the result obtained under random conditions by multiplying the histogram data by each class. Then, the histogram data may be standardized again under the random conditions, so that the direction and the intensity of the abnormal distribution can be simultaneously displayed.

Hence, the difference map 312$j$ of FIG. 27 can display that the particles are concentrated at the periphery as the radius of the radius vector in the horizontal axis is increased compared to the virtual substrates concentrated at the origin. Further, the difference map 312$j$ of FIG. 27 can display that the particles are concentrated at the center as the radius of the radius vector in the horizontal axis is decreased compared to the virtual substrates concentrated at the origin. On the other hand, the polar angle in the vertical axis which is not multiplied by a class is increased compared to the virtual substrates if particles are concentrated regardless of the polar angle of the radius vector.

Further, the display of the particle distribution analysis result is not limited to those shown in FIGS. 9, 11 and 23. The desired information among the determination data, the histogram, the difference map, the ranking map and the like may be selectively displayed by manipulation of the operator.

Although the above embodiment has described the case where the square root of sum of square and the number of intersection points are used as two types of the difference data indicating the difference between the histogram of the target substrate WT and the histograms of the virtual substrate WV1 to WVM, the present disclosure is not limited thereto. By way of example, the sum of arithmetic averages of the histograms and the sum of absolute averages of the histograms may be used as two types of the difference data. Further, among the above-described difference data, a single type of the difference data may be used instead of two types of the difference data.

The present disclosure may be applied to a system including a multiple number of devices or to an apparatus including a single device. It is to be understood that the object of the present disclosure can be achieved by supplying to a system or an apparatus a storage medium storing a program of software that implements the functions of the aforementioned embodiments, and then causing a computer (CPU or MPU) of the apparatus or the system to read out and execute the program stored in the storage medium.

In this case, the program itself read out from the storage medium may implement the functions of the above-mentioned embodiments, and thus, the program and the storage medium storing the program may implement the above-described embodiments. Moreover, the storage medium for storing the program may include such as a Floppy (registered trademark) disk, a hard disk, a magneto-optical disk, an optical disk such as a CD-ROM, a CD-R, a CD-RW, a DVD-ROM, a DVD-RAM, a DVD-RW, or a DVD+RW, a magnetic tape, a non-volatile memory card, or a ROM. Alternatively, the program may be supplied to the computer by downloading it from another computer or database, or a computer (not shown) connected to the Internet, a commercial network, a local area network (LAN) or the like.

Besides, it is to be understood that the functions of each embodiment described above may be implemented by executing the program read by a CPU of the computer, and an OS (operating system) or the like that operated on the CPU may perform a part or all of the actual process in response to instructions of the program and the functions of each embodiment may be implemented by the process.

Furthermore, it is to be understood that the program read from the storage medium may be written in a memory of a function extension board inserted into the computer or a function extension unit connected to the computer, and a CPU of the function extension board or the function extension unit may perform a part or all of the actual process in response to instructions of the program and the function of each embodiment may be implemented by the process.

While various embodiments have been described herein with reference to the accompanying drawings, the present disclosure is not limited thereto. Therefore, it would be understood by those skilled in the art that various changes and modifications may be made within the scope of the accompanying claims and it shall be understood that all changes and modifications are included in the scope of the present disclosure.

The present disclosure is applicable to a support method for a particle distribution analysis for a substrate processed by a substrate processing apparatus, and also applicable to a storage medium for storing a program for executing the same.

What is claimed is:

1. A support method for particle distribution analysis for a substrate, the method comprising:

creating target substrate data by calculating inter-particle distances for all particles on a target substrate subjected to the particle distribution analysis from particle coordinate data of the target substrate, classifying the inter-particle distances into multiple classes, calculating the number of particles in each of the multiple classes, generating a first histogram data indicating the number of particles in each of the multiple classes, and storing the first histogram data in a storage unit;

creating each virtual substrate data for a plurality of virtual substrates each having the same number of randomly distributed particles as the particles on the target substrate by calculating inter-particle distances for all particles on each virtual substrate from particle coordinate data, classifying the inter-particle distances on each virtual substrate into multiple classes, calculating the number of particles in each of the multiple classes for each virtual substrate, generating a second histogram data indicating the number of particles in each of the multiple classes for each virtual substrate, and storing the second histogram data in the storage unit;

creating difference data by calculating an average for the second histogram data of the plurality of virtual substrates and calculating difference data indicating a difference between the first histogram data of the target substrate and the average, and each difference between the second histogram data of each virtual substrate and the average, and storing the difference data in the storage unit;

creating determination data by calculating determination data quantifying a distance between the first histogram data of the target substrate and the second histogram data of the plurality of virtual substrates based on the difference data, and storing the determination data in the storage unit; and displaying the determination data on a display unit.

2. A support method for particle distribution analysis for a substrate performed by a central processing unit (CPU), the method comprising:

creating target substrate data by performed by a central processing unit (CPU) by calculating inter-particle distances for all particles and calculating radiuses and polar angles of radius vectors for particle positions on a target substrate subjected to the particle distribution analysis from particle coordinate data of the target substrate, classifying the inter-particle distances, the radiuses and the polar angles into multiple classes, calculating the number of particles in each of the multiple classes, generating a first histogram data including distance histogram data, radius histogram data and polar angle histogram data indicating the number of particles in each of the multiple classes, and storing the first histogram data in a storage unit;

creating each virtual substrate data for a plurality of virtual substrates each having the same number of randomly distributed particles as the particles on the target substrate by calculating inter-particle distances for all particles on and calculating radiuses and polar angles of radius vectors for particle positions on each virtual substrate from particle coordinate data, classifying the inter-particle distances, the radiuses and the polar angles on the plurality of virtual substrates into multiple classes, calculating the number of particles in each of the multiple classes for each virtual substrate, generating a second histogram data including distance histogram data, radius histogram data and polar angle histogram data indicating the number of particles in each of the multiple classes, and storing the second histogram data in the storage unit;

creating determination data by calculating determination data quantifying a distance between the first histogram data of the target substrate and the second histogram data of the plurality of virtual substrates based on the difference data, and storing the determination data in the storage unit; and displaying the determination data on a display unit.

3. The method of claim 1, wherein the creating difference data includes:

calculating an average and a standard deviation for the number of particles in each of the multiple classes of the second histogram data of the virtual substrates;

standardizing the number of particles in each of the multiple classes of the first and second histogram data of the target substrate and the virtual substrates by using the average and the standard deviation for the number of particles in each of the multiple classes of the second histogram data of the virtual substrates, and generating standardized first and second histogram data of the target substrate and the virtual substrates, and storing the standardized first and second histogram data of the target substrate and the virtual substrates in the storage unit;

calculating the number of intersection points of the particle number and a square root of sum of square of the particle number from the standardized first and second histogram data of the target substrate and the virtual substrates;

calculating an average and a standard deviation of the number of intersection points of the particle number and the square root of sum of square in the standardized second histogram data of the virtual substrates; and standardizing the number of intersection points of the particle number and the square root of sum of square of the particle number of the standardized first and second histogram data of the target substrate and the virtual substrates by using the average and the standard deviation of the standardized second histogram data of the virtual substrates, and storing the standardized number of intersection points of the particle number and the standardized square root of sum of square of the particle number, as the difference data, in the storage unit.

4. The method of claim 1, wherein the creating determination data includes:

calculating a Mahalanobis distance from the difference data and storing the Mahalanobis distance as the determination data in the storage unit.

5. The method of claim 4, wherein the displaying the determination data includes:

displaying the determination data on the display unit, and abnormality of the determination data when the determination data is greater than or equal to a certain threshold value.

6. The method of claim 3, wherein in the displaying the determination data on a display unit, difference data of the number of intersection points between the target substrate and all the virtual substrates, and difference data of the square root of sum of square between the target substrate and all the virtual substrates are respectively plotted on a vertical axis and a horizontal axis, or vice versa.

7. The method of claim 3, wherein in the displaying the determination data on a display unit, difference data of the square root of sum of square calculated from the radiuses between the target substrate and all the virtual substrates, and difference data of the square root of sum of square calculated from the polar angles between the target substrate and all the virtual substrates are respectively plotted on a vertical axis and a horizontal axis, or vice versa.

8. The method of claim 1, wherein in the displaying the determination data on a display unit, each histogram data is generated by calculating the inter-particles distances, and the first histogram data of the target substrate and average second histogram data of the virtual substrates generated by averaging the numbers of each class in the second histogram data of the virtual substrates are displayed on the display unit.

9. The method of claim 2, wherein in the displaying the determination data on a display unit, each histogram data is generated by calculating the radiuses of the radius vectors, and the first histogram data of the target substrate and average second histogram data of the virtual substrates generated by averaging the numbers of each class in the second histogram data of the virtual substrates are displayed on the display unit.

10. The method of claim 2, wherein in the displaying the determination data on a display unit, each histogram data is generated by calculating the polar angles of the radius vectors, and the first histogram data of the target substrate and average second histogram data of the virtual substrates generated by averaging the numbers of each class in the second histogram data of the virtual substrates are displayed on the display unit.

11. The method of claim 2, wherein in the displaying the determination data on a display unit, each histogram data is generated by calculating the radiuses of the radius vectors, and the radiuses of one or more classes, having a large number difference between the first histogram data of the target substrate and average for the second histogram data of the virtual substrates in descending order, in each class of the first histogram data of the target substrate are displayed on a map of the particle coordinate data.

12. The method of claim 2, wherein in the displaying the determination data on a display unit, each histogram data is generated by calculating the polar angles of the radius vectors, and the polar angles of one or more classes, having a large number difference between the first histogram data of the target substrate and average for the second histogram data of the virtual substrates in descending order, in each class of the first histogram data of the target substrate are displayed on a map of the particle coordinate data.

13. A non-transitory computer readable storage medium storing therein a computer program for executing a support method of a particle distribution analysis for a substrate, wherein the support method includes:
creating target substrate data by calculating inter-particle distances for all particles on a target substrate subjected to the particle distribution analysis from particle coordinate data of the target substrate, classifying the inter-particle distances into multiple classes, calculating the number of particles in each of the multiple classes, generating first histogram data indicating the number of particles in each of the multiple classes, and storing the first histogram data in a storage unit;

creating each virtual substrate data for a plurality of virtual substrates each having the same number of randomly distributed particles as the particles on the target substrate by calculating inter-particle distances for all particles on each virtual substrate from particle coordinate data, classifying the inter-particle distances on each virtual substrate into multiple classes, calculating the number of particles in each of the multiple classes for each virtual substrate, generating second histogram data indicating the number of particles in each of the multiple classes for each virtual substrate, and storing the second histogram data in the storage unit;

creating difference data by calculating an average for the second histogram data of the plurality of virtual substrates and calculating difference data indicating a difference between the first histogram data of the target substrate and the average, and each difference between the second histogram data of each virtual substrate and the average, and storing the difference data in the storage unit;

creating determination data by calculating determination data quantifying a distance between the first histogram data of the target substrate and the second histogram data of the plurality of virtual substrates based on the difference data, and storing the determination data in the storage unit; and displaying the determination data on a display unit.

* * * * *

UNITED STATES PATENT AND TRADEMARK OFFICE
CERTIFICATE OF CORRECTION

| | |
|---|---|
| PATENT NO. | : 8,768,644 B2 |
| APPLICATION NO. | : 13/175219 |
| DATED | : July 1, 2014 |
| INVENTOR(S) | : Kunio Miyauchi |

It is certified that error appears in the above-identified patent and that said Letters Patent is hereby corrected as shown below:

In the Specification

Column 17, line 10, replace "5100" with - S100 -

Column 17, line 62, replace "5130" with - S130 -

Column 20, line 6, replace "5350" with - S350 -

Column 22, line 22, replace "5420" with - S420 -

Column 22, line 29, replace "(0)" with - (Φ) -

Column 22, line 52, replace "5530" with - S530 -

Column 23, line 26, replace "5570" with - S570 -

Signed and Sealed this
Seventh Day of October, 2014

Michelle K. Lee
*Deputy Director of the United States Patent and Trademark Office*